(12) United States Patent
Bristol et al.

(10) Patent No.: US 7,858,663 B1
(45) Date of Patent: Dec. 28, 2010

(54) PHYSICAL AND CHEMICAL PROPERTIES OF THYROID HORMONE ORGANIC ACID ADDITION SALTS

(75) Inventors: David William Bristol, Mills River, NC (US); Clifford Riley King, Hendersonville, NC (US); Vicki Haynes Audia, Mills River, NC (US)

(73) Assignee: Pisgah Laboratories, Inc., Pisgah Forest, NC (US)

( * ) Notice: Subject to any disclaimer, the term of this patent is extended or adjusted under 35 U.S.C. 154(b) by 543 days.

(21) Appl. No.: 11/932,336

(22) Filed: Oct. 31, 2007

(51) Int. Cl.
*A61K 31/195* (2006.01)
(52) U.S. Cl. ................................ 514/561
(58) Field of Classification Search .......... 514/561
See application file for complete search history.

(56) References Cited

U.S. PATENT DOCUMENTS

| | | | |
|---|---|---|---|
| 2,925,417 A | 2/1960 | Elslager | 260/240 |
| 3,502,661 A | 3/1970 | Kasubick | 260/240 |
| 5,225,205 A | 7/1993 | Orsolini | 424/489 |
| 5,232,919 A | 8/1993 | Scheffler et al. | 514/212 |
| 5,271,946 A | 12/1993 | Hettche | 424/490 |
| 5,439,688 A | 8/1995 | Orsolini et al. | 424/489 |
| 5,445,832 A | 8/1995 | Orsolini et al. | 424/491 |
| 5,635,209 A | 6/1997 | Groenewoud et al. | 424/464 |
| 5,776,885 A | 7/1998 | Orsolini et al. | 514/2 |
| 5,955,105 A | 9/1999 | Mitra et al. | 424/464 |
| 6,056,975 A | 5/2000 | Mitra et al. | 424/464 |
| 6,114,175 A * | 9/2000 | Klunk et al. | 436/63 |
| 6,190,696 B1 | 2/2001 | Groenewoud | 424/464 |
| 6,242,422 B1 * | 6/2001 | Karanewsky et al. | 514/19 |
| 6,399,101 B1 | 6/2002 | Frontanes et al. | 424/488 |
| 6,491,946 B1 | 12/2002 | Schreder et al. | 424/465 |
| 6,555,581 B1 | 4/2003 | Franz et al. | 514/567 |
| 6,555,591 B1 | 4/2003 | Tomosada et al. | 521/124 |
| 6,627,660 B1 | 9/2003 | Piccariello et al. | 514/567 |
| 7,265,157 B1 * | 9/2007 | Igari et al. | 514/772.1 |
| 7,429,559 B2 * | 9/2008 | Yamamoto et al. | 514/2 |
| 2004/0116522 A1 * | 6/2004 | Yamagata et al. | 514/554 |
| 2005/0250742 A1 * | 11/2005 | Dagostino et al. | 514/80 |
| 2008/0014237 A1 * | 1/2008 | Igari et al. | 424/422 |
| 2008/0249145 A1 * | 10/2008 | Whittock et al. | 514/367 |
| 2009/0005318 A1 * | 1/2009 | Yamamoto et al. | 514/15 |
| 2009/0012124 A1 * | 1/2009 | Wyatt et al. | 514/326 |
| 2009/0124596 A1 * | 5/2009 | Bonnert et al. | 514/211.15 |

FOREIGN PATENT DOCUMENTS

| | | |
|---|---|---|
| EP | 0137600 | 7/1984 |
| FR | 43535 | 6/1934 |
| FR | 1461407 | 12/1966 |
| GB | 295656 | 11/1929 |

OTHER PUBLICATIONS

Hamlin, William E., Northam, Jack I., and Wagner, John G., Relationship Between In Vitro Dissolution Rates and Solubilities of Numerous Compounds Representative of Various Chemical Species, Mar. 31, 1965.

* cited by examiner

*Primary Examiner*—Raymond J Henley, III
(74) *Attorney, Agent, or Firm*—Joseph T. Guy

(57) ABSTRACT

A pharmaceutical composition comprising the salt of a thyroid hormone selected from the group consisting of levothyroxine and liothyronine and an organic acid comprising at least one aromatic ring having at least one hydroxyl moiety and at least one carboxylic acid moiety in an ortho relationship.

167 Claims, 17 Drawing Sheets

PHYSICAL AND CHEMICAL PROPERTIES OF THYROID HORMONE ORGANIC ACID ADDITION SALTS

CROSS-REFERENCE TO RELATED APPLICATIONS

This application is related to co-pending U.S. patent application Ser. No. 11/595,379 filed Nov. 20, 2006, co-pending U.S. patent application Ser. No. 11/843,890 filed Aug. 23, 2007, co-pending U.S. patent application Ser. No. 11/805,225 filed May 22, 2007, co-pending U.S. patent application Ser. No. 11/973,252 filed Oct. 5, 2007 and co-pending patent application Ser. No. 11/928,592 filed Oct. 30, 2007 each of which is incorporated herein by reference.

BACKGROUND OF THE INVENTION

Disclosed herein are compositions and processes for the preparation and use of thyroid hormone derivatives as active pharmaceutical ingredients (APIs) for pharmaceutical compositions. These thyroid hormone derivatives are prepared as their organic acid addition salts which exhibit improved stability compared to the parent compound(s). The instability of the thyroid hormones (of synthetic or animal origin) due to labile aromatic iodine substitution (or other factors) has created formulation, storage and dosing problems for the commercial formulated drug product. The organic acid addition salts described herein exhibit improved stability and handling properties which overcome the existing deficiencies.

Each of the thyroid hormones and related compounds are known by a variety of names ranging from approved International Union of Pure and Applied Chemist (IUPAC) nomenclature to abbreviated naming to facilitate communication. For instance, 3,3',5-triiodothyronine is known as liothyronine, or as T3. Similarly, 3,3'5,5'-tetraiodothyroxine is known as levothyroxine, or as T4. Further, each of these names may be preceded by the appropriate stereochemical indicator for the chiral center contained within the amino acid moiety on each compound. In commerce, the thyroid hormones are most often offered as their alkali metal salt, for instance levothyroxine sodium. These names are not intended to limit the concepts or the scope of the invention presented herein and a more complete listing of names for the thyroid hormones can be found in the Merck Index, 11$^{th}$ Edition under the headings of Liothyronine and under Levothyroxine Sodium. The descriptions herein may use these and other appropriate names interchangeably for each of the thyroid hormones.

Many active pharmaceutical ingredients (APIs) exhibit poor storage stability characteristics due to their chemical or physical response to heat, light, pH, or to oxidative conditions. Further, it is generally recognized that the particular stability profile of a pure API is an intrinsic property of that substance. It is a practical matter that the stability profile of an API be understood, documented and routinely tested on selected manufacturing batches to confirm the process is producing the API with the expected stability profile. The importance of a predictable stability profile, under acceptable storage conditions, cannot be overemphasized when the API will be used in humans. The lack of storage stability and the API's response to degradation stimulators can lead to the lack of drug efficacy, incorrect or ineffective dosage, and undesired, or even deleterious side-effects resulting from impurities generated by degradation pathways. Hence, the determination of a drug substance's stability profile is a well-recognized requirement in the pharmaceutical industry and stability testing is conducted on the API and on the final drug product as the finished dosage form.

Herein a number of terms are used to describe different aspects involved in preparing or establishing the stability of a drug substance and drug product. What is meant by a drug substance is: a molecular entity or compound, also known as an active pharmaceutical ingredient (API) that exhibits biological activity for the purpose of providing human or animal medication to treat disease, pain or any medically diagnosed condition. It is possible for a drug substance to be used in combination with one or more different drug substances to ultimately impart a biological response in humans or animals. A drug substance is typically formulated with other, non-biologically active compounds to provide a means of predictable and quantitative dosage delivery, or perhaps to impart acceptable stability features to the drug product. What is meant by a drug product is: a formulation, mixture or admixture of the drug substance with combinations of excipients, processing aids, buffers and perhaps other inert ingredients that allow delivery of the drug substance by the selected delivery mechanism to the patient at a predictable dosage. Various delivery mechanisms include solid oral dosage, for example, pills, tablets, or capsules. Additional delivery systems can include solution or suspension injection dosage forms (including depo drug products), transdermal patches, and nasal or inhalation devices. The dosage is the actual concentration delivered to the patient, and depending upon many factors and the actual delivery system selected, the dosage may be available for essentially immediate release, release over time, or manipulated by additional means for stimulated release (for example, by irradiation).

The stability profile exhibited by the drug substance in a bulk form and its stability when incorporated into a drug product should be demonstrated and understood. What is meant by the drug substance stability profile is: the analytical evidence of degradation of the drug substance to diminish its assay (and hence, to generate degradation impurities) as the drug substance is exposed over time to degradation stimuli. The analytical testing to determine or confirm the stability profile of the drug substance is routinely conducted on the bulk drug substance and approximately, simultaneously on the drug product containing the drug substance as these entities are subjected to the stability testing regimen. What is meant by stability testing is: the individual storage of the drug product and the drug substance in environmentally controlled chambers maintained at specific humidity and temperature conditions whereby samples of the stored materials can be removed at regular or predetermined intervals, with the samples to be subjected to analytical testing. The results from the analytical testing provide the stability profile of the drug substance and drug product as a function of time and storage conditions. From this data, an expiry date, or shelf-life can be determined such that formulation of drug products with the drug substance can provide commercial products having efficacious and predictable dosage forms eliciting the desired biological response.

For further background, stability testing for a drug substance is often separated into two activities. The first is an investigation to determine the chemical degradation pathway initiated by heat, light, pH or oxidative conditions. Experiments are conducted known as forced degradation studies to intentionally degrade or decompose the drug substance to a sufficient extent that degradation impurities can be assessed by analytical chemical methodology and to demonstrate that the impurities thus generated do not interfere with the quantitative assessment of the remaining, unaltered drug substance. The second activity relies on the results from the degradation investigation and consists of applying standardized exposure conditions adopted by the United States Food and Drug Administration and generally, universally applied to the commercial manufacture of drug substances and drug products. In most instances, the materials (drug substance and product) are subjected to two stability chamber storage conditions to reflect 1) a reasonable temperature and humidity exposure and 2) a more aggressive exposure known as accelerated stability testing. On occasion, a third storage condition at low temperature (approximately 5° C.) is conducted for what is termed pharmaceutical elegance, however this condition provides little meaningful or practical information in most cases. The period of exposure for the reasonable or representative storage condition is used to establish the expiry dating (usually years); the aggressive storage condition is most often a shorter period (months) and can be used as an early warning indicator to potential instability issues. It is noteworthy to state the samples placed into stability storage chambers are packaged identically, as practicably possible, as the enclosure or container device used for the bulk drug substance or the final packaged drug product.

There are other factors that affect the stability of pharmaceutical materials, meaning drug substances or drug products. While it is generally recognized that the stability profile of a pure drug substance is a predictable property of the pharmaceutical material, the overall stability of a molecular entity, compound or drug substance or any formulation with the drug substance, may be impacted by other physical or chemical behavior the drug substance possesses. In this case, pure is defined by comparison to its manufacturing specifications and an assessment by appropriate analytical test procedures using a highly characterized and purified sample as a standard of comparison. The ability to modify these behaviors allows for improvements to the stability profile obtained.

As mentioned above, the forced degradation studies expose the drug substance to heat, light, high and low pH, and oxidative conditions. Often, these studies provide insight into physical or chemical modifications of the drug substance that will improve the stability of the compound. "Martin's Physical Pharmacy and Pharmaceutical Sciences", $5^{th}$ Edition, (Lippincott, Williams & Wilkins publisher); ©2006 authored by Patrick J. Sinko, on page 358 defines pharmacokinetics and pharmacodynamics. Pharmacokinetics is the mathematics of the time course of absorption, distribution, metabolism and excretion (ADME) of drugs in the body. The biologic, physiologic, and physicochemical factors that influence the transfer of those drugs in the body also influence the rate and extent of ADME of those drugs in the body. In many cases, the pharmacologic action and the toxicologic action are related to the plasma concentration of drugs. Through the study and application of pharmacokinetics, the pharmacist can individualize therapy for the patient. Pharmacodynamics is the study of the biochemical physiological effects of drugs and their mechanisms of action. To illustrate this concept, the physical form of the drug substance, perhaps in a solid oral dose application, may determine the pharmacokinetic (PK) profile of the drug substance when used as a drug product in humans or animals. As an example, a drug substance's crystal structure or polymorphic form may impact the bioavailability of the material to the patient. In this case, a manufacturing process may be developed to yield a single crystal form or polymorph providing a predictable PK profile and indeed, it is not unusual that one (or more) polymorphs of a drug substance exhibit an enhanced stability profile compared to other available polymorphs of the identical drug substance. This is an example of manipulating physical properties of the drug substance to provide improved stability characteristics of the active pharmaceutical ingredient and likely, of the commercial pharmaceutical drug product. Similarly, chemical modifications can be implemented that favorably impact the stability profile also. As an example, many hydrochloride or mineral acid salts of drug substances are hydroscopic (also defined as hygroscopic). In this case, the ionic nature of the drug substance (as a salt) may diminish its own stability profile by a host of mechanisms, but for simplicity, the drug substance may have a propensity to absorb water. The water, absorbed from the environment (packaging materials, exposure to air, or in the case of formulated products, from other materials), may lead to degradation products. Hence, the aforementioned description of stability chamber testing at specific temperature and humidity conditions reflects this concern for water leading to degradation products and perhaps, an unacceptable stability profile for the drug substance. A possible chemical modification could include selection of a salt form that does not exhibit hygroscopic properties. Like the previous physical property modification example, changing the salt form may alter the drug substance's PK profile.

Careful attention must be applied such that improving one parameter, such as a drug substance's stability profile, does not adversely alter the desired efficacy when used in a drug product. More specifically, a drug substance's salt form may impact the drug's bioavailability (the rate and location of release, and steady-state concentration) in the body.

As a further illustration of improving a drug substance's stability profile, the selection of a given salt form may eliminate a specific degradation pathway. For instance, some degradation mechanisms are promoted by strong acid conditions, so a drug substance existing as a mineral acid salt may be intrinsically less stable than its weak acid analog. Without adhering to any specific theory or principle, a compound's decomposition as a hydrochloride may be greater than when compared to its decomposition as a citric acid salt and perhaps can be correlated to the relative strength (pKa) of each acid where citric acid is much weaker than hydrochloric acid. The combined effects of acid availability (and strength) through the drug substance's salt form and of the relative propensity of each salt form to absorb water may further delineate which salt form has the preferred stability profile. Consequently, the physical and/or chemical modification of a drug substance may improve its stability profile when subjected to forced degradation studies. However, these improvements, for commercial purposes, should be demonstrated under standardized stability chamber testing at regulated temperature and humidity.

The stability chamber testing serves an additional purpose by evaluating the impact the manufacturing process may have on the stability profile of a given batch of drug substance or drug product. In reality, drug substances and products are manufactured to specifications that represent the best-case scenarios for providing large quantities of acceptable pharmaceutical products to the world's population. Each batch of drug substance is analytically tested for adherence to each specification and is compared to a small, but highly characterized and purified sample of the drug substance known as an analytical standard. This initial testing represents the immediate (non-aged) comparison of the large production batch to the best available material—the analytical standard. Hence, the question arises as to how the manufacturing batch compares to the standard as time passes under given storage conditions. The production batch may contain trace amounts of materials that promote degradation that the analytical standard does not possess. Such trace materials may include intermediates along the synthetic pathway to the drug substance, residual solvents used in the synthesis, or minute traces of metals originating from the actual processing equipment. Individually, or together, these trace amounts of materials may promote the degradation of the drug substance to the extent the stability profile is unacceptable and/or a desired expiry date cannot be attained.

Stability testing, particularly accelerated stability testing is a means to quickly ascertain an API's degradation behavior by a kinetic plot of the assay, impurities and/or degradation impurities as a function of time under the cited conditions. Naturally, the stability profile of an API may be somewhat different when stored as the bulk material under conditions representing a less than optimum controlled environment. For instance, during normal commercial operations an API undergoes various inventory and logistical operations including warehouse storage, shipping and transport, sampling, and the like, wherein excursions from the standardized and laboratory controlled stability testing regimens may occur. During these excursions, the disposition of the API as being fit for use can be called into question. This typically results in analytical re-testing to assure the material it still meets the acceptance specifications. In addition, an understanding of the API's response to real-time storage stability conditions may mitigate or eliminate any potential concerns. Real-time storage stability conditions are defined as storage of the API (or drug product) over an extended period, usually at least one year and perhaps not longer than five years. The storage and handling of the API may be as a bulk sample (e.g. large carton or drum) or a smaller sample representative of the bulk packaging and subjected to the inventory exposure/excursion conditions the bulk API may undergo. A typical example of an exposure condition bulk API may experience is a container being partially used during manufacture of the final dose product. In this scenario, bulk API is exposed to an environment (perhaps a controlled environment), but it is then re-sealed and returned to inventory. Another common environmental exposure of bulk API occurs during routine removal of an analytical test sample from the bulk material. Real-time stability storage information provides business and technical management with insight into how to best manage the bulk API for its long-term stability and efficacy when formulated into a drug product. For drug products employing particularly low dosages of the API, such as the thyroid hormones, an understanding of the API's real-time storage stability assists in assuring the correct amount of the API is obtained in the dosage presentation. Real-time storage stability also allows for insight into how quickly, and under what conditions, drug product manufacturing must occur to assure the correct dosage is obtained in the drug product. Consequently, laboratory samples and API lot retains provide meaningful technical information to assess API stability under a host of conditions for which commercial bulk API may be exposed.

Practically, pamoic acid has received very little attention either by pharmaceutical scientists or synthetic organic chemists. Two simplistic observations are recurring themes in the folklore (i.e. industry practice or belief) surrounding pamoic acid derivatives. In general, the preparation of a pamoate salt converts a liquid material to a solid and an improved organoleptic property has been ascribed to such salts. Organoleptic properties, for example, are smell and taste, and pamoate salts of drug substances have been suggested as eliminating the bitter taste compared with other salts (or free base) of the drug substance.

The ability to form salts is a technique routinely employed by the practicing organic chemist. The methodology is used to separate and purify materials since many active pharmaceutical ingredients can be isolated and recrystallized as their salt with a concomitant improvement to their stability profile. It is a matter of in-depth experimentation, particularly for pharmaceutical materials, to identify which salt will optimize a complex set of variables. The salt selected may impact the drug substance's synthesis, synthesis yield, and the ability to purify the drug substance. The salt prepared will have intrinsic physical and chemical properties that impact its stability profile, pharmacokinetic behavior, formulation stability, ease of manufacturing into a final dose drug product (for instance the ability to obtain blend uniformity, or a tablet stable to mechanical manipulations), bioavailability, solubility and its basic efficacy and therapeutic selectivity. Individually or in combination inventive solutions are required, since a priori predictions to these considerations or to secondary influences such as the salt's steric bulk, relative pKa and pKb of the acid and base components respectively, the degree of association between the acid and base components (for example the use of acid or base components that are bi-, or multiple-dentate and have the ability to form tight complexes with its conjugate) are insufficient to guarantee a desired outcome. Truly, the factors are too numerous to successfully predict an outcome independent of experimental data.

While salt formation is a routinely practiced technique, the selection or identification of which salt to prepare requires a rigorous inventive contribution to obtain a material meeting a complex set of requirements. These requirements, as alluded to previously include an entire chain of events that begins with drug substance manufacturing (synthesis, isolation, purification and characterization), drug product formulation and manufacturing (appropriate for the desired delivery system or device), demonstration of the actual therapeutic value, and the event chain never completely ends because of an on-going stability testing program long after all the drug product has entered the marketplace. As a first approach to meeting this barrage of requirements, the selection of an appropriate salt of the active pharmaceutical ingredient involves a combination of observation, experience and analysis of the structural characteristics of the active ingredient.

After selecting and preparing perhaps several potential candidates (different salts of the drug substance) for initial screening, forced degradation studies and analytical methodology development ensues. Recall that the forced degradation studies are the first steps in evaluating the stability of the selected candidates and have the purpose of deliberately degrading the material to a sufficient extent to observe degradation impurities. This activity further serves the analytical method development effort to identify techniques useful for observing the impurities without interfering with a quantitative measurement of the salt candidate. The analytical techniques employed are inherently chromatographic methodologies (e.g. HPLC, MPLC, GC, TLC) capable of separating complex mixtures into their components. After the initial degradation study, one or more salt candidates may remain suitable for further development.

As a further complication, the initial degradation studies and subsequent stability testing may be complicated by the selected salt candidates' ability to exhibit polymorphism. This property of a compound is its ability to solidify in different crystal structures called polymorphs. Indeed, for a drug substance that exhibits polymorphism, different situations may exist: the material may solidify and be isolated from the reaction as 1) an amorphous solid; 2) a single polymorph may be obtained, or 3) a mixture of polymorphs and 4) combinations of the previous three possibilities. Therefore it is important, when polymorphism is suspected, to deliberately attempt to prepare, isolate and characterize the different polymorphs by techniques sufficient to differentiate between amorphous material and individual polymorphs or their mixtures. Often differential scanning calorimetry (DSC), infrared spectrophotometric analysis, particularly Fourier Transform infrared spectroscopy (FTIR), and powder X-ray diffraction (PXRD) are employed to identify or monitor the creation of polymorphs.

API salts and polymorphs often exhibit different solubility characteristics, for instance rate of dissolution with a pH dependence, and therefore yield a different pharmacokinetic profile and/or therapeutic efficacy. Sometimes, a given drug product formulation expertise or technology can dominate any biological effects the API salt and/or polymorph present. Conversely, drug product formulation and the resulting mechanical properties of a tablet, capsule or bead can be dominated by the physical behavior of the API salt and/or its particular crystal structure. It is not unusual that difficult trade-offs must be made between the ease of manufacture of the drug product and the pharmacokinetics desired.

Concurrent to the pharmacokinetic response desired from formulation techniques, the formulator must address and accommodate the characteristics of the API salt to achieve robust manufacturing processes for the drug product. For instance, the mechanical properties of tablets are influenced by the API salt's physical (and sometimes chemical) characteristics. API salts are often milled to specific particle size ranges to achieve a host of desired features, including but not limited to, blend uniformity of the formulation and enhanced bioavailability (larger surface area available to aid is solubility of moderately insoluble API salts). Tablet mechanical properties, such as hardness, friability, compressive strength, resistance to abrasion, dissolution, and the like can all be impacted by the API salt's physical characteristics. While this example is provided for solid oral dose formulations, other delivery methodologies include but are not limited to injection (solution or suspension), transdermal patches, inhalation devices, and the like, each have their mechanical delivery requirements to implement and deliver a chemical dosage to humans. The formulator often has a difficult task in simultaneously achieving robust manufacturing formulations and expected pharmacokinetic responses. Additionally, the formulator must demonstrate the delivery mechanism and the drug product formulation, combined, have an acceptable stability profile. An interesting complication to these requirements is encountered more frequently as API development and drug discovery has advanced to provide highly potent APIs, and where chemically available, API salts. The overall therapeutic effectiveness of these new drugs is radically increasing and often, the required per unit dosage is very small. It poses significant manufacturing difficulties to weigh or otherwise measure very small quantities of extremely potent drug substances and to achieve formulations that have robust manufacturing processes, with homogenous blend uniformity and that statistically provide a discrete unit dosage per delivery mechanism (e.g. same dosage per tablet).

The prior art indicates significant effort in addressing the stability deficiencies of the thyroid hormones in formulated pharmaceutical compositions. Essentially, two approaches are undertaken, a) improve the stability of the drug substance used in the formulation, or b) impart stability to the drug substance by formulation of the drug product in which the thyroid hormone is used. The former approach is illustrated in U.S. Pat. No. 6,627,660 [Piccariello, et al.], the disclosure of which is totally incorporated herein by reference, discloses dialkylphosphinate protecting groups for the phenolic hydroxyl moiety of thyroxine compounds that prevents a proposed decomposition pathway from occurring. It is suggested that the protecting group prevents the spontaneous tautomerization of T4 that ultimately leads to its decomposition to diiodotyrosine (DIT) and iodoquinone.

Alternatively, several approaches to improving thyroid hormone stability are illustrated in the following patents ostensibly by mechanisms involving the encapsulation of the hormone(s) into a stabilized matrix form, or by providing a common ion effect to eliminate decomposition pathways involving the aryl iodine substitutions. U.S. Pat. No. 6,555,591 [Franz, et al.], the disclosure of which is totally incorporated herein by reference, discloses stabilized pharmaceutical compositions that by formulation methodology using microcrystalline cellulose particles, improves the stability of the thyroid hormone drugs, levothyroxine sodium and liothyronine sodium.

U.S. Pat. No. 6,555,581 B1 [Franz, et al.], the disclosure of which is totally incorporated herein by reference, discloses levothyroxine (T4) and liothyronine (T3) pharmaceutical compositions and the associated methods for preparing immediate release and stabilized formulations.

Similarly, U.S. Pat. No. 6,491,946 B1 [Schreder et al.], the disclosure of which is totally incorporated herein by reference, discloses a pharmaceutical preparation of levothyroxine absent antioxidants and further auxiliaries and processes for preparing same.

U.S. Pat. No. 6,399,101 [Frontanes, et al.], the disclosure of which is totally incorporated herein by reference, discloses stabilized pharmaceutical compositions that by formulation methodology using silicified microcrystalline cellulose, improves the stability of the thyroid hormone drug, levothyroxine sodium.

U.S. Pat. No. 6,190,696 [Groenewoud] the disclosure of which is totally incorporated herein by reference, discloses stabilized pharmaceutical compositions that by formulation methodology using one or more iodine salts or iodine donor compounds, improves the shelf-life stability of thyroxine medications and their combinations.

U.S. Pat. No. 6,056,975 [Mitra, et al.], the disclosure of which is totally incorporated herein by reference, discloses stabilized pharmaceutical compositions that by formulation methodology using a proscribed carbohydrate possessing the characteristic property of a water soluble glucose polymer, improves the stability of the thyroid hormone drug, levothyroxine sodium.

U.S. Pat. No. 5,955,105 [Mitra, et al.], the disclosure of which is totally incorporated herein by reference, discloses stabilized pharmaceutical compositions that by formulation methodology using a proscribed carbohydrate possessing the characteristic property of a water soluble glucose polymer, and a soluble or insoluble cellulose polymer, improves the stability of the thyroid hormone drug, levothyroxine sodium.

U.S. Pat. No. 5,635,209 [Groenewoud, et al.], the disclosure of which is totally incorporated herein by reference, discloses a stabilized pharmaceutical composition that by formulation methodology uses potassium iodide, acting as a stabilizing excipient, improves the stability of the thyroid hormone drug levothyroxine sodium.

It is of some historical interest that the pamoate salts of a variety of active pharmaceutical ingredients have received attention, noting that an embonate salt is identical to a pamoate salt. In the following cited literature, the pamoate was apparently chosen a) for converting a liquid active pharmaceutical ingredient into a solid, b) for eliminating the bitter taste associated with many active pharmaceutical ingredients, or c) as a process for isolating and then chemically characterizing otherwise difficult to delineate alkaloids or active pharmaceutical ingredients. For instance, U.S. Pat. No. 5,232,919 [Scheffler, et al.], the disclosure of which is totally incorporated herein by reference, discloses azelastine embonate and pharmaceutical formulations/compositions which contain it; said embonate salt to eliminate the bitter taste of azelastine alone.

Further, the French Patent 1,461,407 [Saias, et al.], the disclosure of which is totally incorporated herein by reference, discloses a process for the preparation of amine pamoates where the amine component includes piperazine, promethazine, papaverine, pholocodine, codeine, noracotine and chlorpheniramine.

The United Kingdom Patent Specification [295,656, Carpmaels & Ransford, agents for applicants] the disclosure of which is totally incorporated herein by reference, discloses a process for the manufacture of difficulty soluble salts of organic bases and alkaloids. The disclosure further indicates the process for manufacture provides sparingly soluble and tasteless salts of organic nitrogenous basic compounds including alkaloids.

U.S. Pat. No. 3,502,661 [Kasubick, et al.], the disclosure of which is totally incorporated herein by reference, discloses a process for the preparation of variously substituted pyridinium and imidazolines along with their acid addition salts. Some examples indicate pamoate salts were prepared for select organic bases.

U.S. Pat. No. 2,925,417 [Elslager, et al.], the disclosure of which is totally incorporated herein by reference, discloses quinolinium salts of pamoic acid and a process for their manufacture.

Lastly, the following cited literature indicates the incorporation of pamoate salts in pharmaceutical formulations for providing the controlled release of water insoluble polypeptides or the oil soluble azelastine. Hence, U.S. Pat. No. 5,776,885 [Orsolini, et al.], the disclosure of which is totally incorporated herein by reference, discloses a pharmaceutical composition for the sustained and controlled release of water insoluble polypeptides whereby the therapeutically active peptide is in the form of its pamoate, tannate or stearate salt.

U.S. Pat. No. 5,445,832 [Orsolini, et al.], the disclosure of which is totally incorporated herein by reference, discloses a process for the preparation of microspheres made of a biodegradable polymeric material whereby a water soluble peptide or peptide salt is converted into a corresponding water-insoluble peptide salt selected from pamoates, stearates or palmitates of the said peptide.

U.S. Pat. No. 5,439,688 [Orsolini, et al.], the disclosure of which is totally incorporated herein by reference, discloses a process for preparing a pharmaceutical composition in the form of microparticles designed for the controlled release of a drug that includes a biodegradable polymer and where the active ingredient can be selected from a group of possible salts, one being a pamoate.

U.S. Pat. No. 5,271,946 [Hettche] the disclosure of which is totally incorporated herein by reference, discloses a controlled release azelastine containing pharmaceutical composition whereby azelastine is incorporated into the formulation as its pamoate or other pharmaceutically active salt.

U.S. Pat. No. 5,225,205 [Orsolini, et al.], the disclosure of which is totally incorporated herein by reference, discloses a pharmaceutical composition in the form of microparticles; the formulation consisting of a peptide as its pamoate, tannate, stearate or palmitate salt; the formulation to provide a controlled release, pharmaceutical composition for the prolonged release of a medicamentous substance.

Formulated drug products containing thyroid hormones have received intense scrutiny from the US Food and Drug Administration (FDA) over the past decade. In particular, the FDA's responsibility for protecting the US population by reviewing and assuring that only safe and efficacious drug products are commercially available, has led the FDA to reassess the approval process of the thyroid hormones, specifically levothyroxine containing products. Synthroid is a commercial drug product containing levothyroxine and has been available for US consumption for decades. With increased reports on the instability and difficulty in obtaining efficacious dosage forms, the FDA instituted a requirement that Synthroid be subjected to the current regulatory approval process as if it were a new drug. The FDA announced on Aug. 14, 1997 via the Federal Register (62 FR 43535) that levothyroxine sodium in oral dosage presentations constitute "new drugs" and that the continued marketing of these products must comply with the new drug application (NDA) approval process. The intention was an NDA submission would necessitate final dose manufacturers to perform the statistical experimentation required to demonstrate long-term stability of the drug product, a uniform and consistent dosage per tablet, and consequently, that patients would receive the proper therapeutic dosage of a life-saving drug. The FDA mandate has created considerable market "disturbance" and essentially because of regulatory pressures Synthroid was ultimately purchased and transferred from one company to another. The new owners of the drug product filed an NDA and received the FDA's approval. Excerpted verbatim from the FDA's "Review and Evaluation of Pharmacology/Toxicology Data" for the new drug application NDA 21-210 and in regard to unapproved products is the following:

"One problem with currently marketed formulations is a lack of stability and batch to batch reliability."

Despite gaining regulatory acceptance via the New Drug Application, the drug product and the drug substance have inherent technical challenges primarily due to the instability of the API. The commercial aspects for Synthroid and related thyroid hormone products to supplement or replace Synthroid are in excess of $500 million US dollars. Hence, the motivation to correct and improve deficiencies in the current products and their precursor APIs, albeit in addition to those already addressed by the FDA's indomitable spirit for protecting the public, is substantial.

On Oct. 3, 2007, the U.S. Food and Drug Administration released the following notice: "FDA Acts to Ensure Thyroid Drugs Don't Lose Potency Before Expiration Date". As such, the FDA has issued letters to all new drug application (NDA) and abbreviated new drug application (ANDA) holders requiring that they change the product specification on levothyroxine sodium products to meet a 95% to 105% potency specification throughout the product's labeled shelf-life. Formerly, the accepted specification was 90-110%. The new specification is a challenging goal to which manufacturers of levothyroxine products must submit a Supplement to their (A)NDA within eighteen months and with the expectation the revised potency specification implemented into commercial operations within twenty-four months.

SUMMARY OF THE INVENTION

The current invention addresses an unmet need in the marketplace by providing stable thyroid hormone organic acid addition salts that can be formulated to uniform and stable oral dosage forms of drug product.

An embodiment of the invention is provided in a pharmaceutical composition comprising the salt of a thyroid hormone selected from the group consisting of levothyroxine and liothyronine and an organic acid comprising at least one aromatic ring having at least one hydroxyl moiety and at least one carboxylic acid moiety in an ortho relationship.

Another embodiment is provided in a method of administering a thyroid hormone. The method includes:

forming a drug substance comprising a salt of a thyroid hormone selected from the group consisting of levothyroxine and liothyronine and an organic acid comprising at least one aromatic ring having at least one hydroxyl moiety and at least one carboxylic acid moiety in an ortho relationship;

incorporating said drug substance into a drug product wherein said drug product has 25-300 μg of said thyroid hormone and a molar ratio of said thyroid hormone to said organic acid of at least 0.9:1 to no more than 2.1:1; and providing said drug product to a patient.

Yet another embodiment is provided in a method of manufacturing a drug substance as a stable thyroid treatment comprising:

combining a thyroid hormone with a predetermined first stoichiometric ratio of an organic acid salt comprising at least one aromatic ring having at least one hydroxyl moiety and at least one carboxylic acid moiety in an ortho relationship thereby forming a thyroid hormone salt;

storing said thyroid hormone salt for a predetermined time thereby forming an aged drug substance; and determining a second stoichiometric ratio of said thyroid hormone and said organic acid salt in said aged drug substance.

Yet another embodiment is provided in a method of manufacturing a drug product as a stable thyroid treatment comprising:

combining a thyroid hormone with a predetermined first stoichiometric ratio of organic acid salt comprising at least one aromatic ring having at least one hydroxyl moiety and at least one carboxylic acid moiety, both in an ortho or vicinal relationship thereby forming a thyroid hormone salt;

forming a drug product comprising said thyroid hormone salt;

storing said drug product for a predetermined time thereby forming an aged drug product; and determining a second stoichiometric ratio of said thyroid hormone and said organic acid salt in said aged drug product.

Yet another embodiment is provided in a process for the preparation of an organic acid salt of a thyroid hormone comprising the steps of:

preparing a first mixture comprising an alkali earth salt, free base or mineral acid salt of said thyroid hormone;

preparing an organic acid mixture wherein said organic acid comprises at least one aromatic ring substituted with at least one hydroxyl group and at least one carboxyl group in an ortho relationship to one another, combining said first mixture and said organic acid mixture wherein said thyroid hormone and said aromatic acid form said organic acid salt of a thyroid hormone; isolating said organic acid salt of a thyroid hormone by at least one method selected from filtration, centrifugation and solvent evaporation; and purifying said organic acid salt of a thyroid hormone by at least one method selected from recrystallization and chromatographic separation.

Yet another embodiment is provided in a process for the preparation of a purified thyroid hormone comprising the steps of:

obtaining a first mixture comprising at least one thyroid hormone selected from liothyronine and levothyroxine;

reacting said first mixture with an organic acid wherein said organic acid comprises at least one aromatic ring substituted with at least one hydroxyl group and at least one carboxyl group in an ortho relationship to one another thereby forming an organic acid salt of said thyroid hormone.

Yet another embodiment is provided in a pharmaceutical composition comprising the salt of a thyroid hormone selected from the group consisting of levothyroxine and liothyronine and an a stoichiometric amount of an organic acid comprising at least one aromatic ring having at least one hydroxyl moiety and at least one carboxylic acid moiety in an ortho relationship wherein said salt is stable for at least one year to variations in at least one of water content, heat, light, oxidative conditions and pH changes as indicated by said stoichiometric amount varying by less than 5% as measured by chromatographic techniques.

DESCRIPTION OF THE INVENTION

Figure 1:
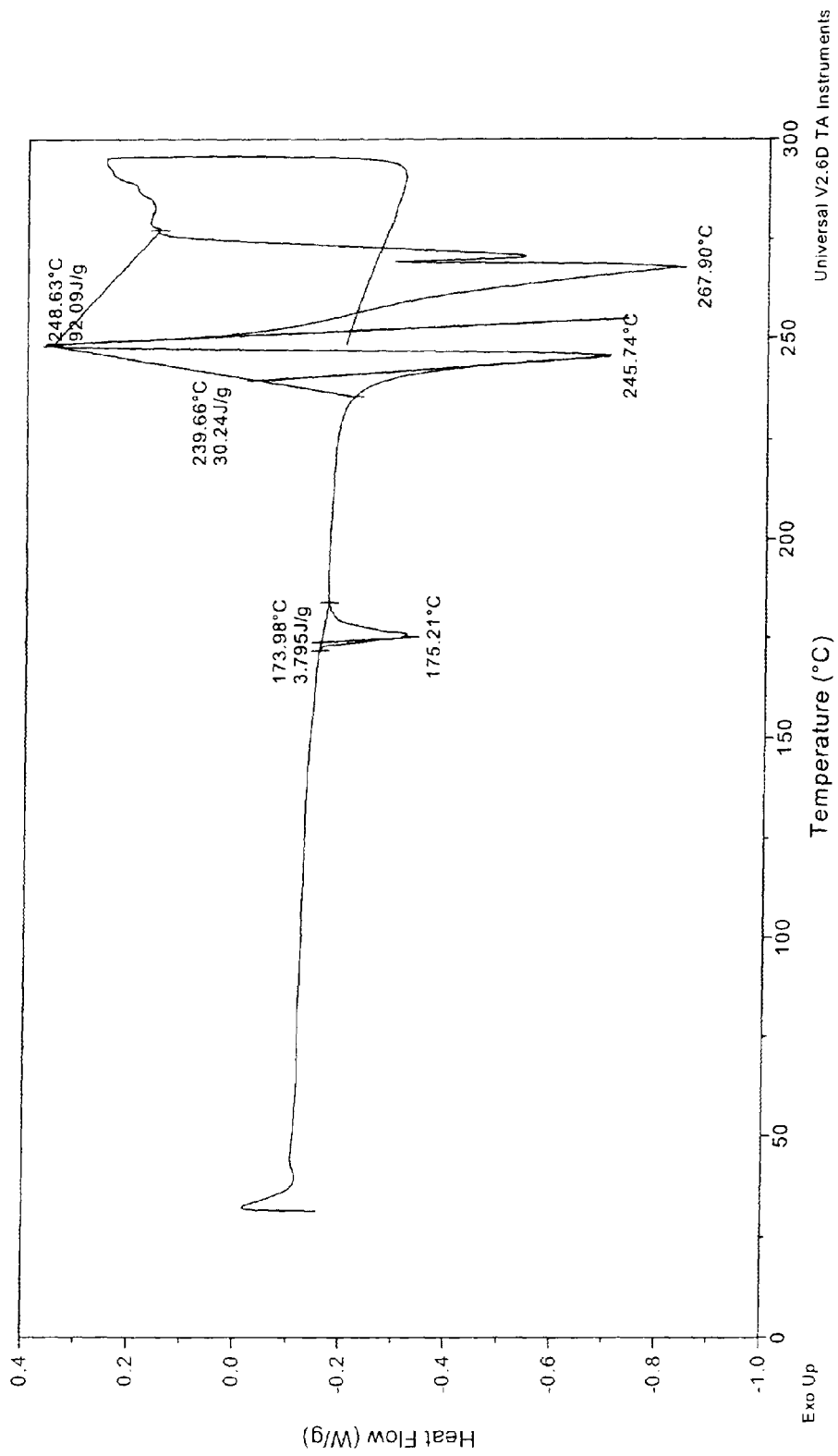
FIG. 1 is a differential scanning calorimetry (DSC) thermogram of liothyronine pamoate.

The invention described herein involves the formation of a salt via reaction of the amine functionality contained within the thyroid hormone and an organic acid or an organic acid salt to yield a comparatively large, bulky compound compared to inorganic salts of the thyroid hormones. However, the organic acid salt may be prepared by reacting the carboxylic acid moiety with an inorganic base such as sodium hydroxide, potassium hydroxide, lithium hydroxide and combinations, or a comparatively low molecular weight amine (less than 500 molecular weight units), including but not limited to, ammonia, triethyl amine, trimethyl amine, methyldiethyl amine and the like, or in combination with amines and inorganic bases. The selection of a low molecular weight amine to provide a counterion to the carboxylate salt of the organic acid is to allow for ease of removal when preparing the targeted salt between the thyroid hormone and the organic acid component.

The reaction of levothyroxine and/or liothyronine with an organic acid whereby the organic acid contains at least one aromatic ring having at least one hydroxyl moiety and at least one carboxylic acid moiety, both in an ortho or vicinal relationship to one another forms the amino moiety of the thyroid hormones with an organic acid counterion. The reaction is conducted in a manner to prevent thermal decomposition of the resulting, insoluble salt in the reaction medium. Further, the resulting organic acid salt of the thyroid hormone possesses increased stability and resistance to thermal, photochemical, oxidative and variable pH decomposition pathways compared to the parent compound or inorganic salts of individual hormones. Optionally, where the organic acid defined above contains more than one carboxylic acid and vicinal hydroxyl moiety, the reaction stoichiometry can be adjusted to yield more than one equivalent of the thyroid hormone (T3 or T4) per molecule of salt formed. Such instances are available when the carboxylic acid employed is pamoic acid, also known as embonic acid, and their appropriate salts, e.g. disodium pamoate.

The traditional sodium or alkali metal salts of the thyroid hormones, like levothyroxine sodium, possess sufficient hygroscopic characteristics which contribute to their observed instability in final dose products containing the API. Without holding to any specific theory or principle, it is observed that the organic content, for instance, of the pamoate residue within a thyroid hormone salt of same provides sufficient lipophilic character to make the new (bulk) salts less hygroscopic. In addition, the lipophilic nature of the hormones' aromatic iodine substitution is accentuated as the tyrosine residue (amino acid zwitterionic character) is tightly bound as the organic acid addition salt. Isolation of the bis-thyroid hormone pamoate salt and its subsequent purification is thereby enhanced without compromising its stability.

Indeed, the reduced hygroscopicity enhances the ability to isolate and purify the thyroid hormone(s) as their organic acid salt and potentially, decreases the thermal exposure the thyroid hormone may receive if isolated as a conventional sodium salt found in commerce. For instance, levothyroxine sodium is a water-soluble compound whereas levothyroxine as a pamoic acid salt is insoluble. Therefore, isolation of the sodium salt from an aqueous solution would require water removal; a process that subjects the compound to energy intensive processing, or to expensive techniques such as lyophilization (freeze drying). Fortunately, other pamoate salts of commerce (which possess water insolubility) have exhibited sufficient physiological solubility to have therapeutic utility as medications. Hence, the water insolubility of the thyroid hormone pamoates provides an enhanced stability and manufacturing feature without detriment to bioavailability in formulated drug products.

In a preferred embodiment of the invention, the organic acid selected for reaction with the thyroid hormone(s) is pamoic acid or alternatively, disodium pamoate. Other inorganic or low molecular weight amine salts of pamoic acid are also suitable for preparing the desired hormone salts. Pamoic acid, or a salt form such as disodium pamoate, is characterized by having two aromatic rings each possessing in an ortho or 1,2 relationship an hydroxyl group and a carboxyl residue. The stoichiometry allows for two equivalents of thyroid hormone to be reacted with one mole of pamoic acid (or its salt, e.g. disodium pamoate), to provide a compound having two thyroid hormone residues for every pamoic acid moiety. Typically, these compounds are water insoluble, or only slightly water soluble and are easily isolated from water reaction medium.

Besides pamoate salts, other organic acid salts can be prepared which provide the beneficial features of the invention. The organic acids suitable to employ the invention are defined by the following Structures A through G wherein Structure A represents the general family of compounds embodied within the invention. Structure B represents the subset of salicylic acid and its derivatives conceived as a component of this invention. Structures C, D and E are regio-isomeric variations on Compound A wherein two adjacent substituents on Compound A form a fused aryl ring (i.e. $R^1+R^2$; $R^2+R^3$; and $R^3+R^4$). Structures F and G represent a further sub-category of dimer-like compounds derived from Structure A. In Structure F, dimerization has occurred through $R^4$ of two Structure A compounds with both possessing fused-aryl ring systems formed via $R^2+R^3$. In Structure G, dimerization has again occurred through $R^4$ of two Structure A compounds however both Structure A residues possess fused-aryl ring systems formed via $R^1+R^2$.

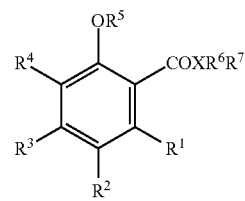

Structure A wherein $R^1$-$R^4$ are independently selected from H, alkyl of 1-6 carbons, adjacent groups may be taken together to form a cyclic alkyl or cyclic aryl moiety; $R^5$ represents H, alkyl, alkylacyl or arylacyl; $R^6$ and $R^7$ are independently selected from H, alkyl of 1-6 carbons, aryl of 6-12 carbons, alkylacyl or arylacyl analogues sufficient to satisfy the valence of X (e.g. to provide a mixed anhydride or carbamate); X is selected from nitrogen, oxygen or sulfur, and when X=O, $R^6+R^7$ may represent an alkali earth cation, ammonium or together form a heterocyclic moiety.

Particularly preferred organic acids include Structures B through E.

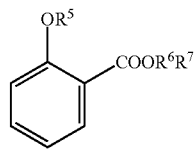

Structure B wherein $R^5$, $R^6$ and $R^7$ remain as defined above for Structure A;

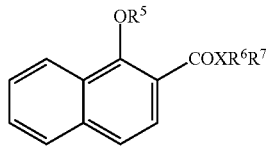

Structure C wherein X, $R^5$, $R^6$ and $R^7$ remain as defined above for Structure A and more preferably X is O;

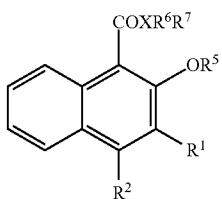

Structure D wherein X, $R^1$, $R^2$, $R^5$, $R^6$ and $R^7$ remain as defined above for Structure A and more preferably X is O; $R^1$ and $R^2$ are hydrogen;

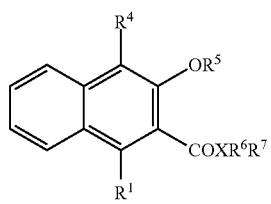

Structure E wherein X, $R^1$, $R^4$, $R^5$, $R^6$ and $R^7$ remain as defined above for Structure A and more preferably X is O, $R^1$ and $R^4$ are hydrogen;

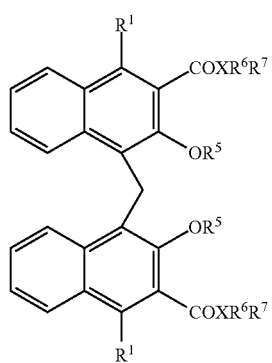

Structure F wherein X, $R^1$, $R^5$, $R^6$ and $R^7$ are independently defined as above for Structure A and more preferably at least one X is O and at least one $R^1$ is hydrogen; and

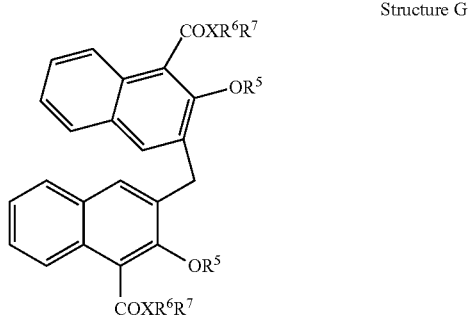

Structure G wherein X, $R^5$, $R^6$ and $R^7$ are independently defined as above for Structure A and more preferably X is O and $R^5$ is hydrogen.

Throughout the instant description the terms organic acid, organic salt, organic moiety, organic counterion and the like are used interchangeably. The organic salt referred to by formulas A-G may be a counterion to an API or present as a free material as an acid, salt, or other form as set forth above.

Pamoic acid, or a synthetic equivalent of pamoic acid, is the preferred embodiment. Pamoic acid has a formula corresponding to Structure F wherein X is O; $R^5$, $R^6$ and $R^7$ are hydrogen.

A synthetic equivalent of pamoic acid is a material that provides the structural moiety independent of its particular salt, ester, or amide form and that upon pH adjustment yields pamoate functionality suitable for reaction, optionally with one or two equivalents of an amine-containing active pharmaceutical ingredient to form a pamoate salt. More preferably the molar ratio of organic moiety to active pharmaceutical ingredient is at least about 1:1 to no more than about 2.2:1 and most preferably either 1:1 or 2:1. Examples of synthetic equivalents of pamoic acid capable of manipulation to produce pamoate salts include but are not limited to, disodium pamoate, di-ammonium pamoate, di-potassium pamoate, lower molecular weight di-alkyl and/or di-aryl amine pamoate, lower molecular weight di-alkyl and/or di-aryl esters of pamoic acid, and lower molecular weight di-alkylacyl and/or di-arylacyl O-esters of pamoic acid, i.e. those alkylacyl and arylacyl esters formed using the hydroxyl moiety of pamoic acid and not the carboxylic acid functional group. The descriptor phrase "lower molecular weight" used above means the indicated moiety has a molecular mass contribution within the pamoate derivative of less than about 200 amu.

For clarity, the use of lower molecular weight di-alkyl or di-aryl amine pamoate allows for the exchange of higher molecular weight amines, or drug free bases, to be exchanged for the lower molecular weight amine component during the salt formation reaction. Similarly, the use of lower molecular weight di-alkylacyl and/or di-arylacyl pamoates allow for their conversion through ester hydrolysis to the pamoic/pamoate moiety followed by reaction with the desired drug free base.

In a specific embodiment of the invention, two equivalents of levothyroxine sodium were reacted with one mole of disodium pamoate to produce the bis-levothyroxine pamoate. However, the organic acid addition salt of the thyroid hormones will be defined according to the available stoichiometry of the organic acid, or upon the salt actually isolated during its preparation. Consequently, it should be recognized that the thyroid hormones could exist as the 2:1 or 1:1 pamoate salts, whereas salts prepared of the salicylate family or similar organic acids would, by stoichiometry, be 1:1 salts. The new salt is produced by reaction through the amine functionality within the tyrosine residue of levothyroxine. This amine is part of an amino acid residue (tyrosine) and the remaining acid moiety on levothyroxine may remain as its sodium salt or be converted to any other permissible salt for which organic carboxylic acids may form (of an inorganic or organic nature and combinations thereof). In one embodiment, the carboxylic acid residue of discussion may exist as an organic acid ester.

In another embodiment of the invention, two equivalents of liothyronine sodium were reacted with one mole of disodium pamoate to produce the bis-levothyroxine pamoate. The new salt is produced by reaction through the amine functionality within the tyrosine residue of liothyronine. This amine is part of an amino acid residue (tyrosine) and the remaining acid moiety on liothyronine may remain as its sodium salt or be converted to any other permissible salt for which organic carboxylic acids may form (of an inorganic or organic nature and combinations thereof). In one embodiment, the carboxylic acid residue of the liothyronine may exist as an organic acid ester.

A major feature of this invention is to resolve a difficult instability issue concerning the use and formulation of thyroid hormones for commercial drug products. Another feature of the invention is to provide stable organic acid salt forms of levothyroxine and liothyronine. Yet another feature of the invention is to provide stable salt forms of the thyroid hormones of molecular weights more than double the current APIs employed. The advantage of the molecular weight feature is to reduce weighing errors in dosage forms by allowing a higher mass to be used to reach the same effective dosage obtained with the lower molecular weight salts. For example, levothyroxine sodium has a molecular weight of about 799. The bis-levothyroxine pamoate disodium salt has a molecular weight of about 1986. The bis-levothyroxine pamoate disodium salt provides two equivalents of levothyroxine to a formulated dosage form. Hence, by calculation to adjust for the number of levothyroxine molecules delivered and to account for the difference in molecular weight of the salt forms, approximately 24% more bis-levothyroxine pamoate disodium salt would be added to a dosage formulation to achieve the same level of levothyroxine. For the very small dosages used in thyroid hormone therapies (standard dosage ranges are from 25-300 micrograms per tablet according to the Physicians' Desk Reference, 54$^{th}$ Edition, 2000, page 1513), an additional 24% mass required through the present invention is a significant manufacturing benefit. At the lower dosage levels, blend uniformity, dosage consistency and the actual analytical chemistry methods employed to assure the correct amount of API is in each tablet are challenged. When employing the invention described herein, the additional mass used in formulation to provide an equivalent dosage, reduces the statistical variability from the drug product manufacturing process. Together, the additional stability feature and the increased mass per unit dosage provide substantial reductions in variability for assessing the API's quality and that of the final dosage form.

Yet another feature of the invention is its ability to be used in conjunction with other drug stabilizing technologies. As mentioned vide supra, a) improve the stability of the drug substance used in the formulation, or b) impart stability to the drug substance by formulation of the drug product in which the thyroid hormone is used. The present invention is applicable to techniques to improve the stability of the drug substance through pro-drug synthesis or derivatization (e.g. Piccariello), or through formulation efforts employing 1) matrix technologies which isolate the active ingredient within the formulation, or 2) excipients which may shift the equilibrium degradation pathway to the preferred stable state (e.g. Groenewoud).

The features of the present invention also include mixtures of the two thyroid hormones wherein independently or together, each may be present as an organic acid addition salt and/or may be used in conjunction with mineral acid salts, or as the metal salt of the carboxylic acid moiety on the tyrosine residue.

The dissolution properties manifested by the organic acid addition salts found in co-pending application [King, et al.], indicate the thyroid hormone addition salts herein provide a mechanism for immediate release, controlled release, extended release and targeted release formulated drug products.

The levothyroxine and liothyronine organic acid addition salts herein are useful as replacement or supplemental therapy in patients with hypothyroidism of any etiology; as pituitary thyroid-stimulating hormone suppressants, as diagnostic agents in suppression tests to differentiate suspected mild hyperthyroidism or thyroid gland autonomy.

The organic acid addition salts of levothyroxine described herein are useful in the oral treatment/replacement therapy in patients exhibiting conditions characterized by diminished or absent thyroid function, e.g. cretinism, myxedema, nontoxic goiter, or hypothyroidism. In addition, the material may be used to suppress thyrotropin secretion in the management of simple nonendemic goiter, chronic lymphocytic thyroiditis, and thyroid cancer.

The organic acid addition salts of the present invention provide an immediate and necessary commercial benefit in the preparation of life-sustaining drug products. In addition, a feature of the present invention is the applicability of the United States Food and Drug Administration's 505(b)(2) regulatory submission process for new drug applications.

The organic acid addition salts of the present invention exhibit significant resistance to degradation pathways with ambient stability achievable for at least four years.

The organic acid addition salts of the present invention possess a stability tracking marker which serves as an internal standard for assessing the quality of either the bulk active ingredient or formulated dosage products. By way of example, the pamoate counterion of these thyroid hormones described herein is a stable, non-hygroscopic material possessing a chromophore. Chromatographic analysis of the active ingredient pamoate salt as a function of time allows for a direct assessment of the assay and impurity levels within the bulk drug substance or formulated product. The results of these analyses provide the stability profile of the drug substance (in bulk) or as formulated products.

The present invention provides for a method to isolate thyroid hormones from fermentation broths, semi-synthetic or synthetic processes, particularly those processes employing aqueous solvents and/or mixtures of aqueous and water-miscible organic solvents. For example, the insolubility of the pamoate salts at relevant processing pH provides for the precipitation of the organic acid addition salt from these solution environments.

Throughout the disclosure the terms 1:1 and 2:1 refer to the nominal molar ratio of active pharmaceutical ingredient and counterion which is defined to be within the normal manufacturing tolerance. Therefore, any reference to 1:1 is inclusive of ratios between about 0.95:1 and about 1.05:1. Similarly, any reference to 2:1 is inclusive of ratios between about 1.95:1 and about 2.05:1. Stoichiometric ratio and molar ratio are used interchangeably herein.

Throughout the disclosure all measurements are done at ambient temperatures and pressures in aqueous solution unless otherwise specified. Any reference to an physiological conditions refer to standard physiological properties including temperature and pH in unless otherwise specified.

Specific experimental embodiments will now be described in detail. These examples are intended to be illustrative and the claims are not limited to the materials, conditions, or process parameters set forth in these embodiments. All parts and percentages are by weight unless otherwise indicated.

EXPERIMENTAL

Differential Scanning Calorimetry (DSC)

Samples were evaluated using a Differential Scanning Calorimeter from TA Instruments (DSC 2010). Prior to analysis of samples, a single-point calibration of the TA Instruments DSC 2010 Differential Scanning Calorimeter (DSC 2010) with the element indium as calibration standard (156.6±0.25° C.) was completed.

Fourier Transform Infrared Spectroscopy (FTIR)

IR Spectra were obtained in a KBr disc using a Perkin Elmer Spectrum BX Fourier Transform Infrared Spectrophotometer. Instrument calibration was performed using a NIST traceable polystyrene standard. Spectra were obtained over the frequency range of 4000 to 600 $cm^{-1}$ with 32 scans per minute, 4 $cm^{-1}$ resolution at 2 $cm^{-1}$ intervals. For the purposes of demonstrating the present invention infrared spectra are formed by mixing the sample with potassium bromide. The pamoate (~8-12 mg/~8-14% wt/wt) was loaded to dry KBr (~100-120 mg) then mixed (mortar/pestle). A portion of this mixture was compressed in a die by employing a minimum amount of pressure to form a thin, and suitably transparent disc. A blank KBr disc was also prepared and its spectrum subtracted from that of the sample pamoate.

Powder X-Ray Diffraction (PXRD)

Powder X-Ray diffraction patterns were acquired on a Scintag XDS2000 powder diffractometer using a copper source and a germanium detector.

HPLC analyses were performed on a Waters Breeze 1525 Binary HPLC Pump chromatograph using a Waters 2487 Dual λ Absorbance Detector.

Proton Nuclear Magnetic Resonance Spectroscopy ($^1$H NMR)

Proton NMR spectra were obtained on a JEOL 500 MHz NMR with samples prepared as solutions in DMSO-$d_6$.

Example 1

Preparation of Liothyronine Pamoate

Figure 2:
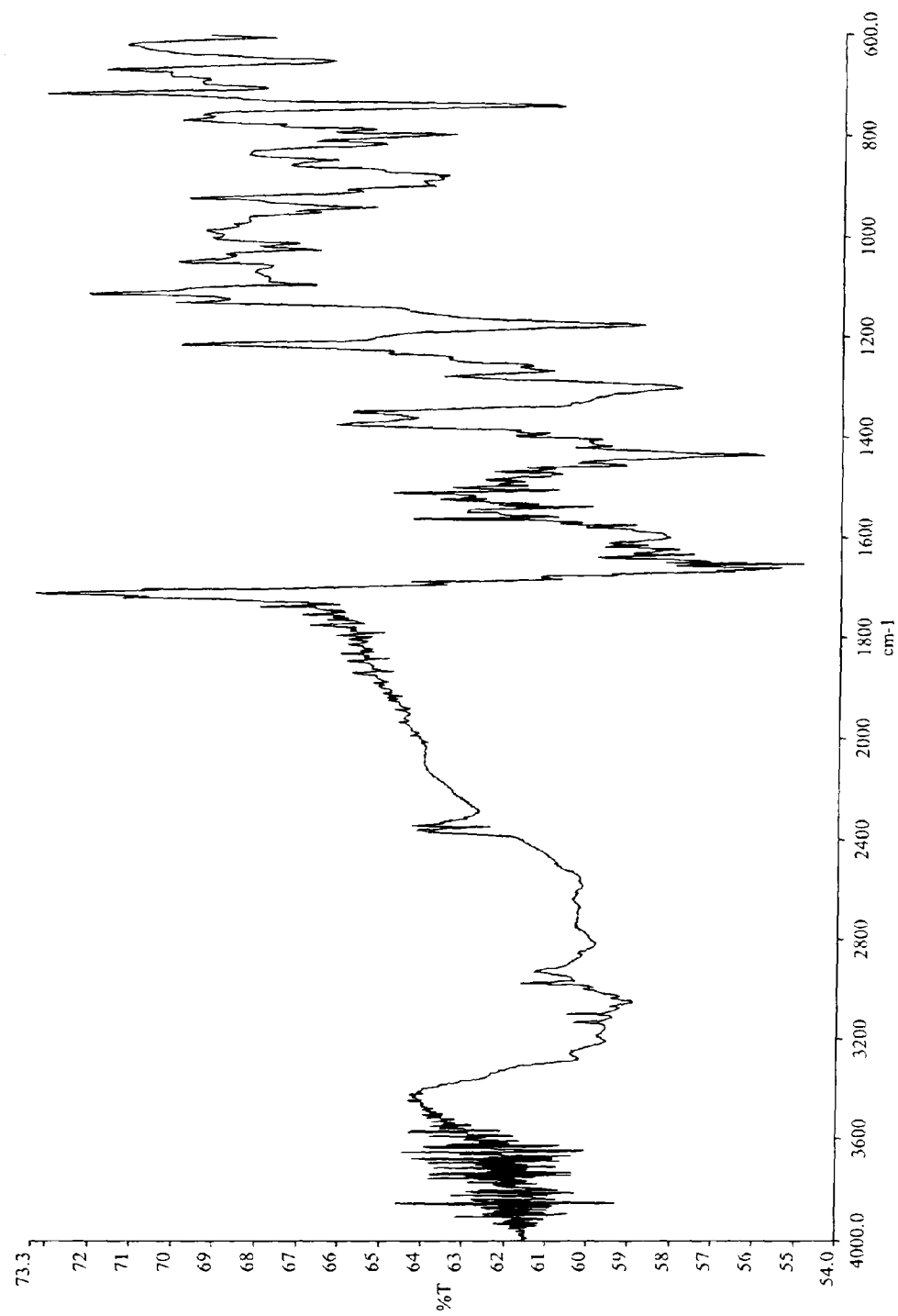
FIG. 2 is a Fourier Transform Infrared (FTIR) spectrum of liothyronine pamoate.
Figure 3:
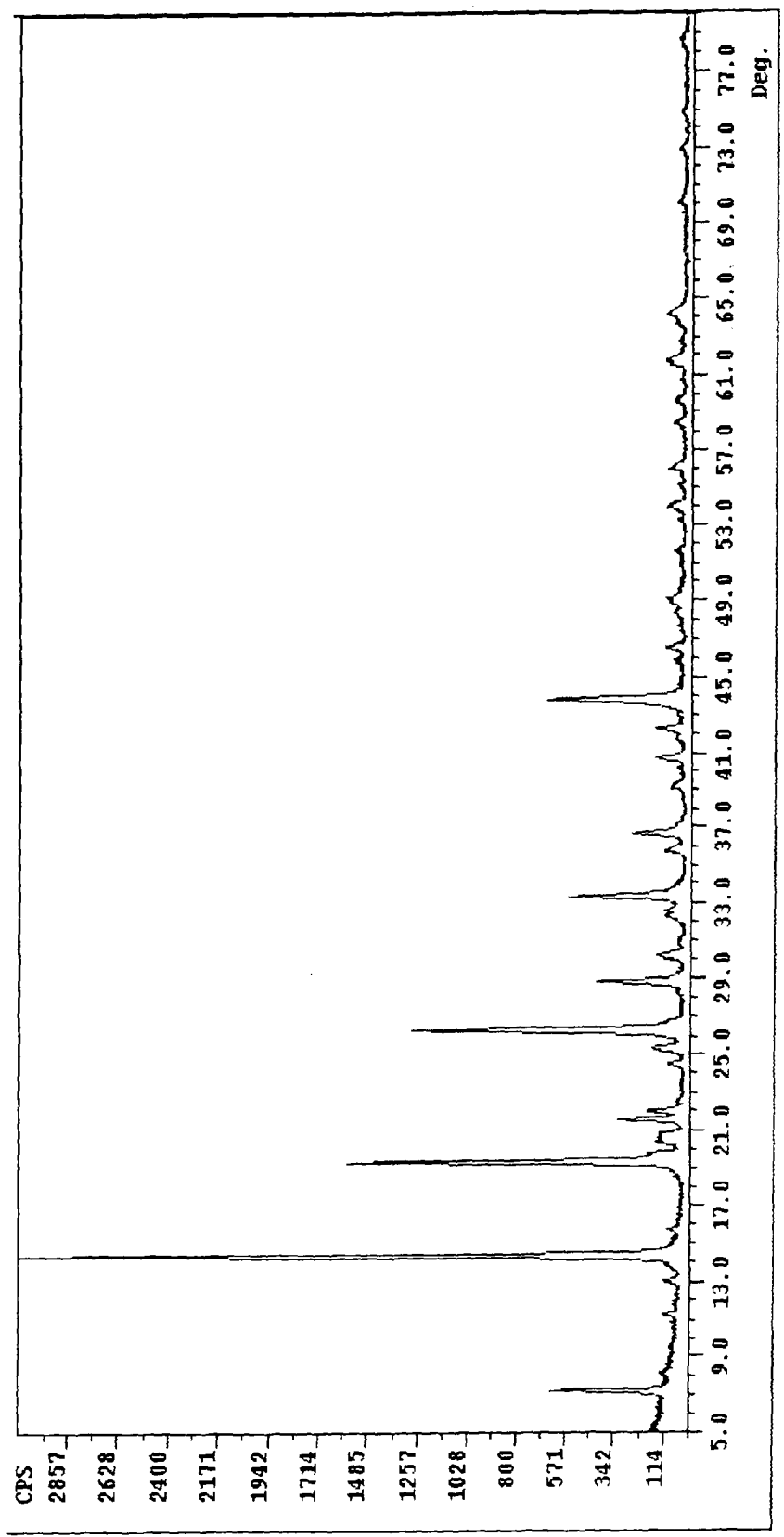
FIG. 3 is a Powder X-Ray Diffraction (PXRD) diffractogram of liothyronine pamoate.
Figure 4:
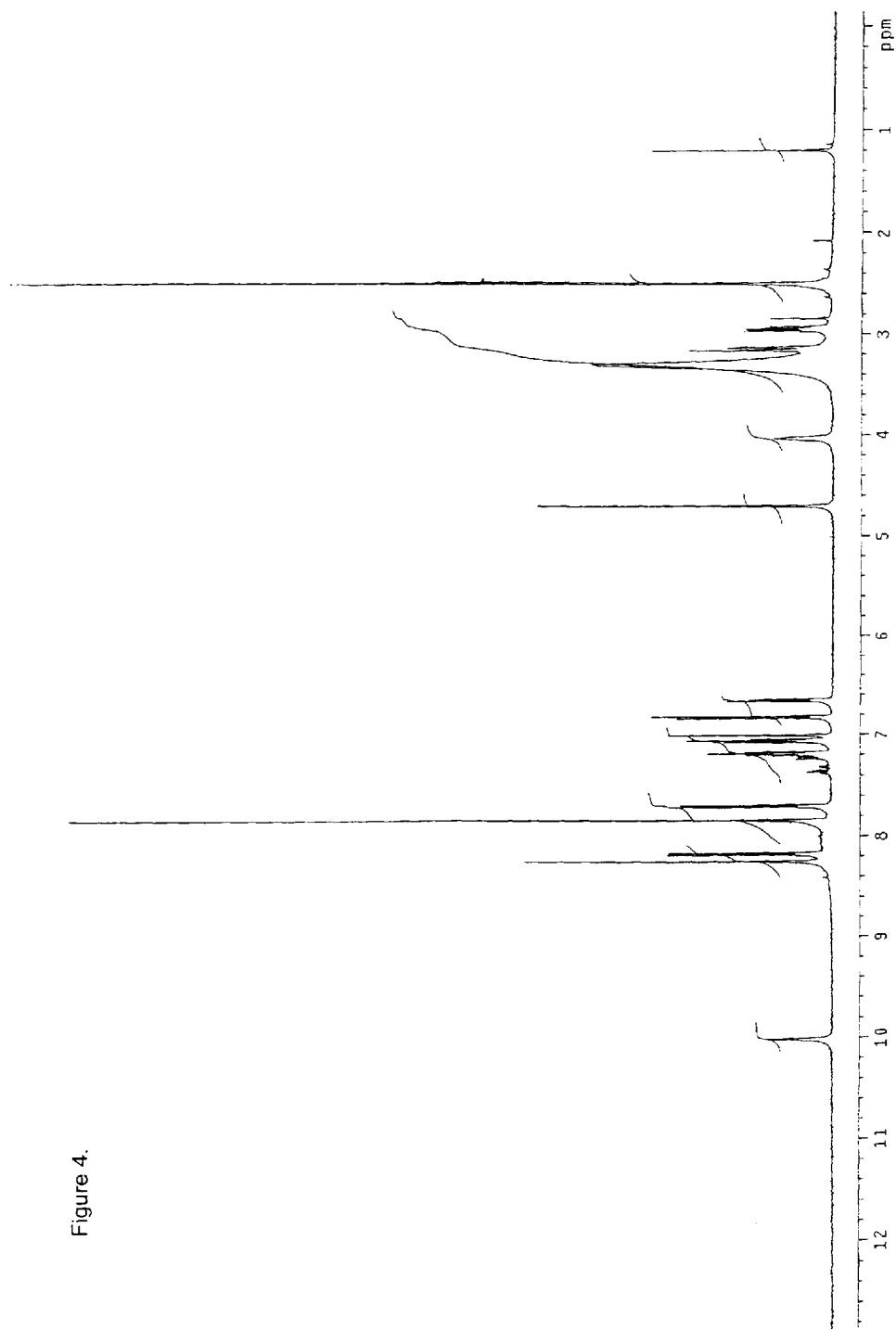
FIG. 4 is proton nuclear magnetic resonance ($^1$H NMR) spectrum of liothyronine pamoate.
Figure 5:
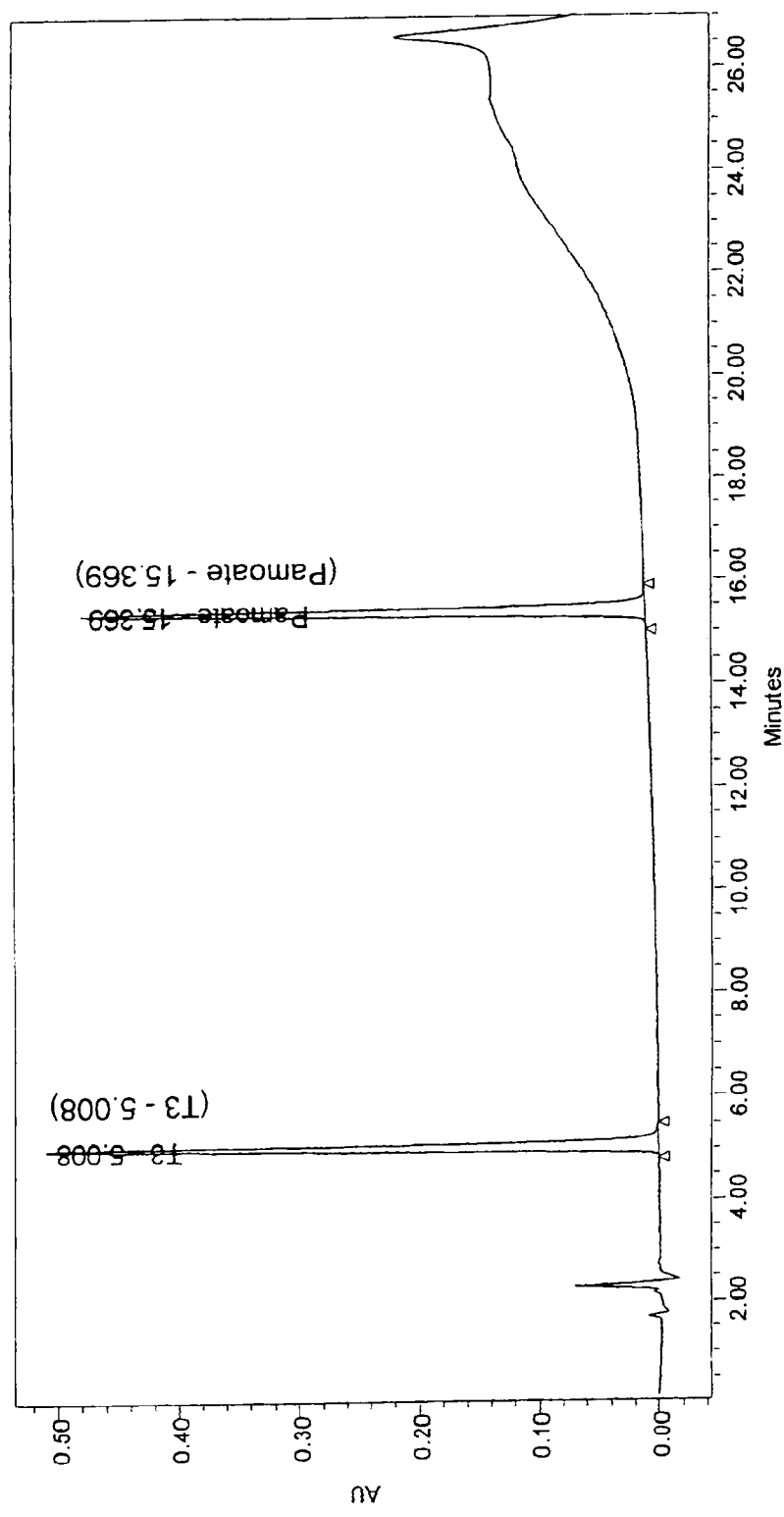
FIG. 5 is an high pressure liquid chromatograph (HPLC) chromatogram of freshly prepared liothyronine pamoate.

To $T_3$ (51.44 g, 79.0 mmol) in methanol (300.00 g) as a mixture was added 1N HCl (80.0 mL, 80.0 mmol). Additional methanol (500.0 g) was added to the mixture to achieve an opaque solution. The opaque solution was filtered (GF/B 55 mm) to clarify and clear the solution. In a separate flask, disodium pamoate (17.80 g, 17.08 dry, 4.2% $H_2O$, 39.5 mmol) in USP water (320.0 g) was stirred at pH 10.7. HCl (0.02 N, 12 mL) was added to adjust the solution to about pH 9.2. at about 20° C. The T3/HCl/CH$_3$OH solution (~151 g) was transferred via metered addition funnel to the disodium pamoate solution (pH 9.20) at about 20-22° C. over approximately 2.5h. Immediate precipitation of tan-yellow solids was observed. After complete addition, the mixture was stirred for about 45 min. Solids were collected by filtration (125 mm Büchner, Qual 4). Solids were washed with USP water (200 g×4) and dried on Büchner under $N_2$ blanket for about 2.5 hours. Yellow solids (124.9 g) were transferred to a drying dish and dried under vacuum at 42-44° C. with $N_2$ sweep (18" Hg) (47% LOD). After 22 h, solids were removed from the oven, broken up and returned to oven. Final liothyronine pamoate (65.64 g, 98.3%) was transferred to an amber jar and stored cold. The material was characterized by DSC (FIG. 1), FTIR (FIG. 2), PXRD (FIG. 3), $^1$H NMR (FIG. 4) and HPLC (FIG. 5).

Example 2

Preparation of Levothyroxine Pamoate

Figure 9:
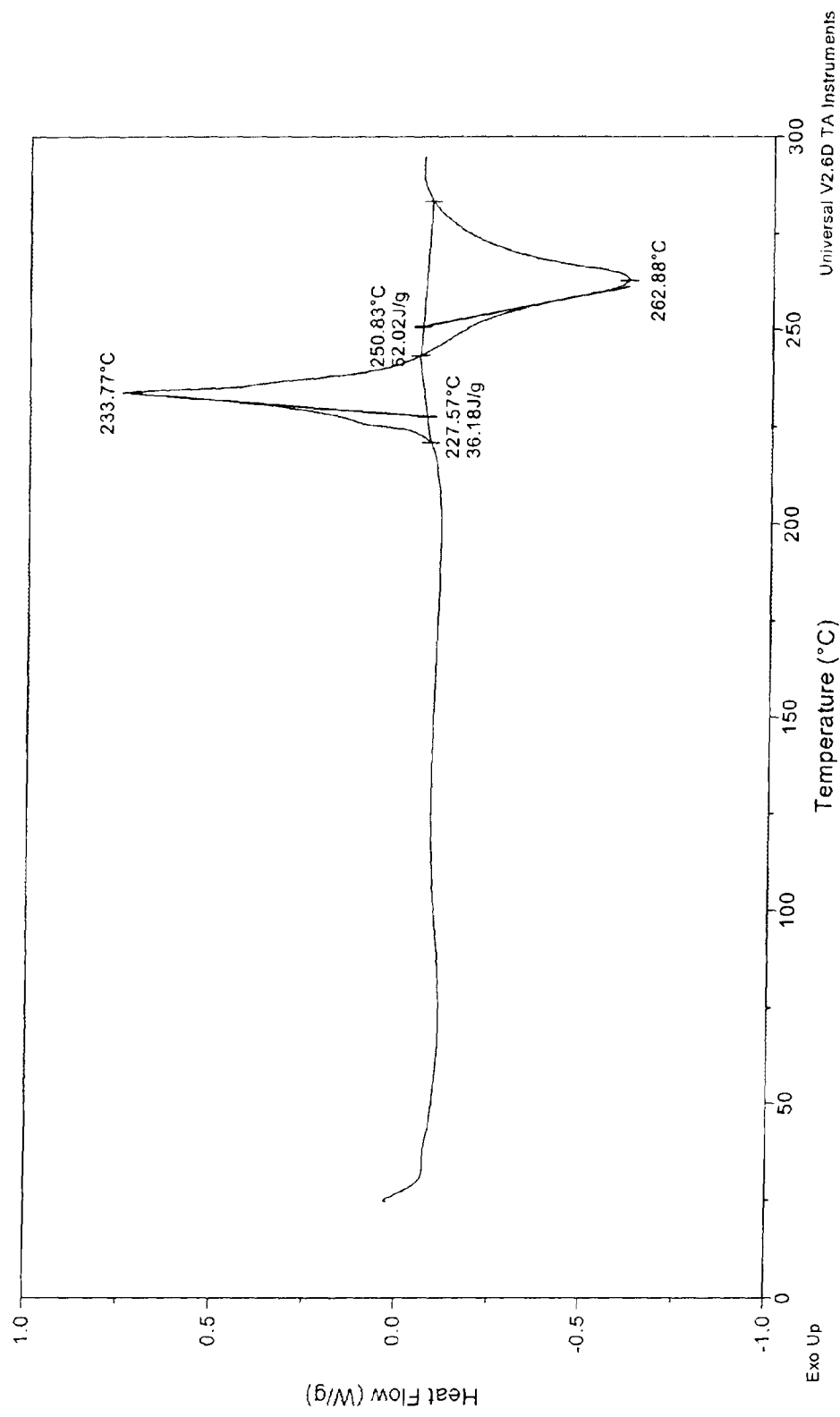
FIG. 9 is a differential scanning calorimetry (DSC) thermogram of levothyroxine pamoate.
Figure 10:
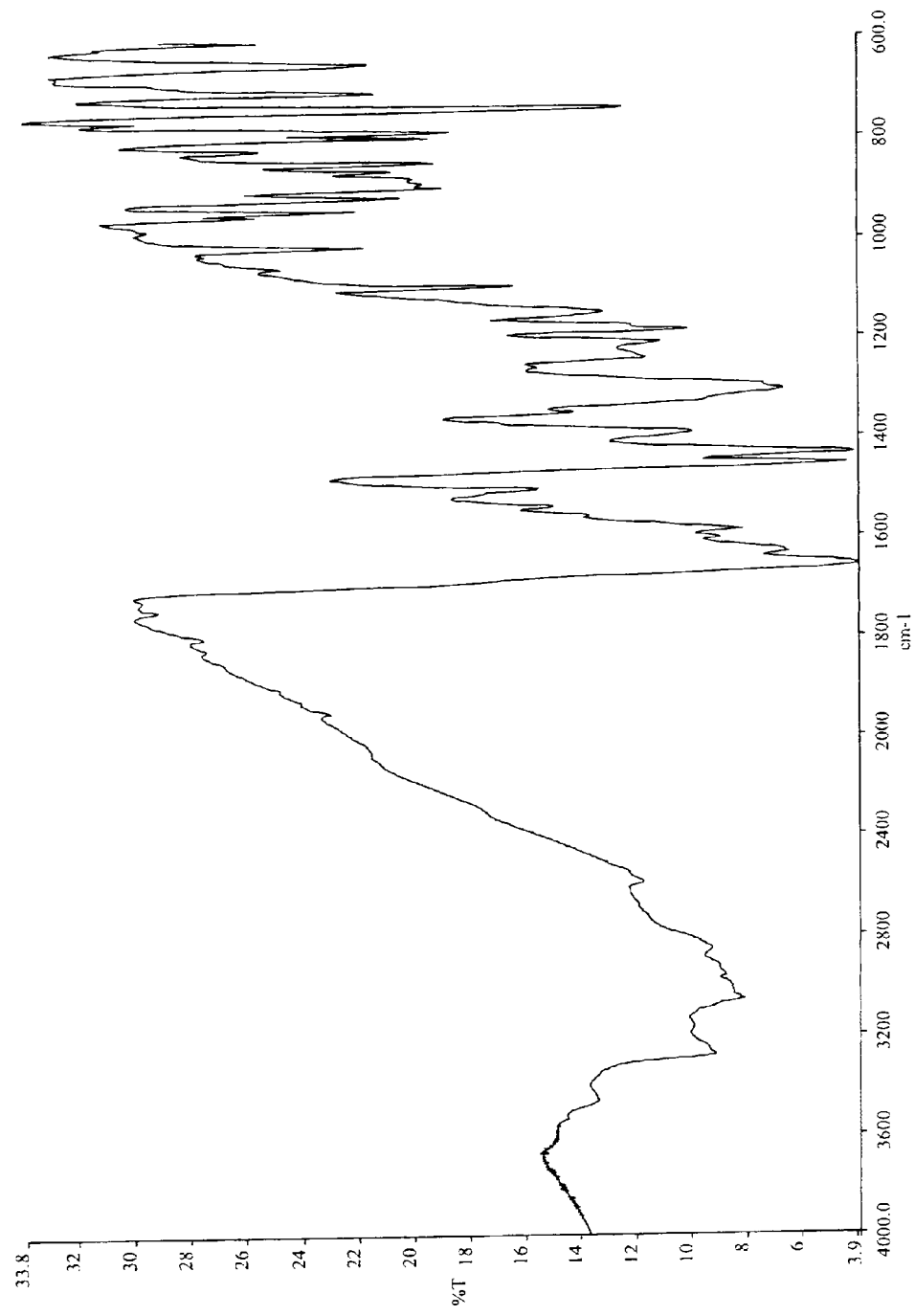
FIG. 10 is a Fourier Transform Infrared (FTIR) spectrum of levothyroxine pamoate.
Figure 11:
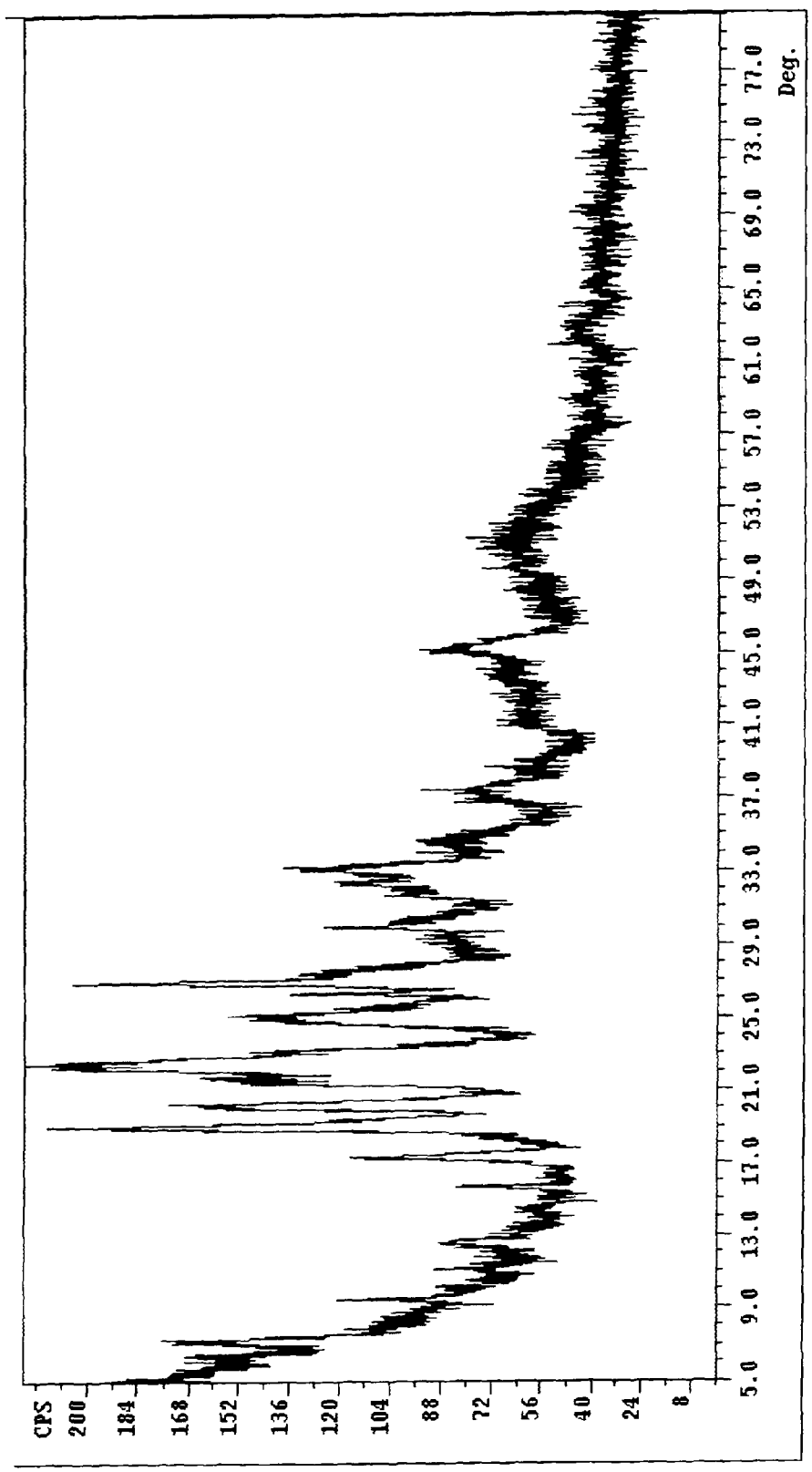
FIG. 11 is a Powder X-Ray Diffraction (PXRD) diffractogram of levothyroxine pamoate.
Figure 12:
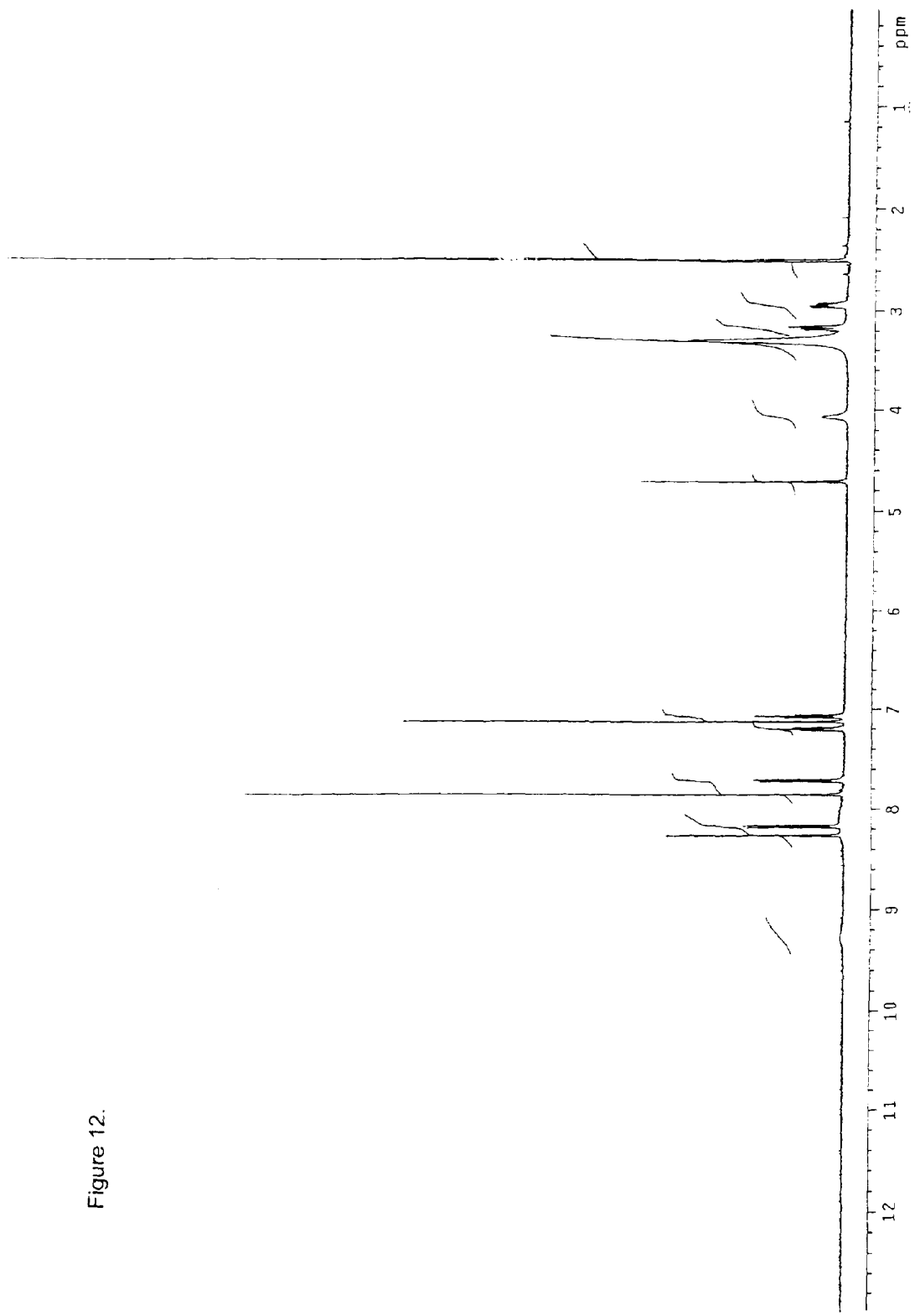
FIG. 12 is proton nuclear magnetic resonance ($^1$H NMR) spectrum of levothyroxine pamoate.
Figure 13:
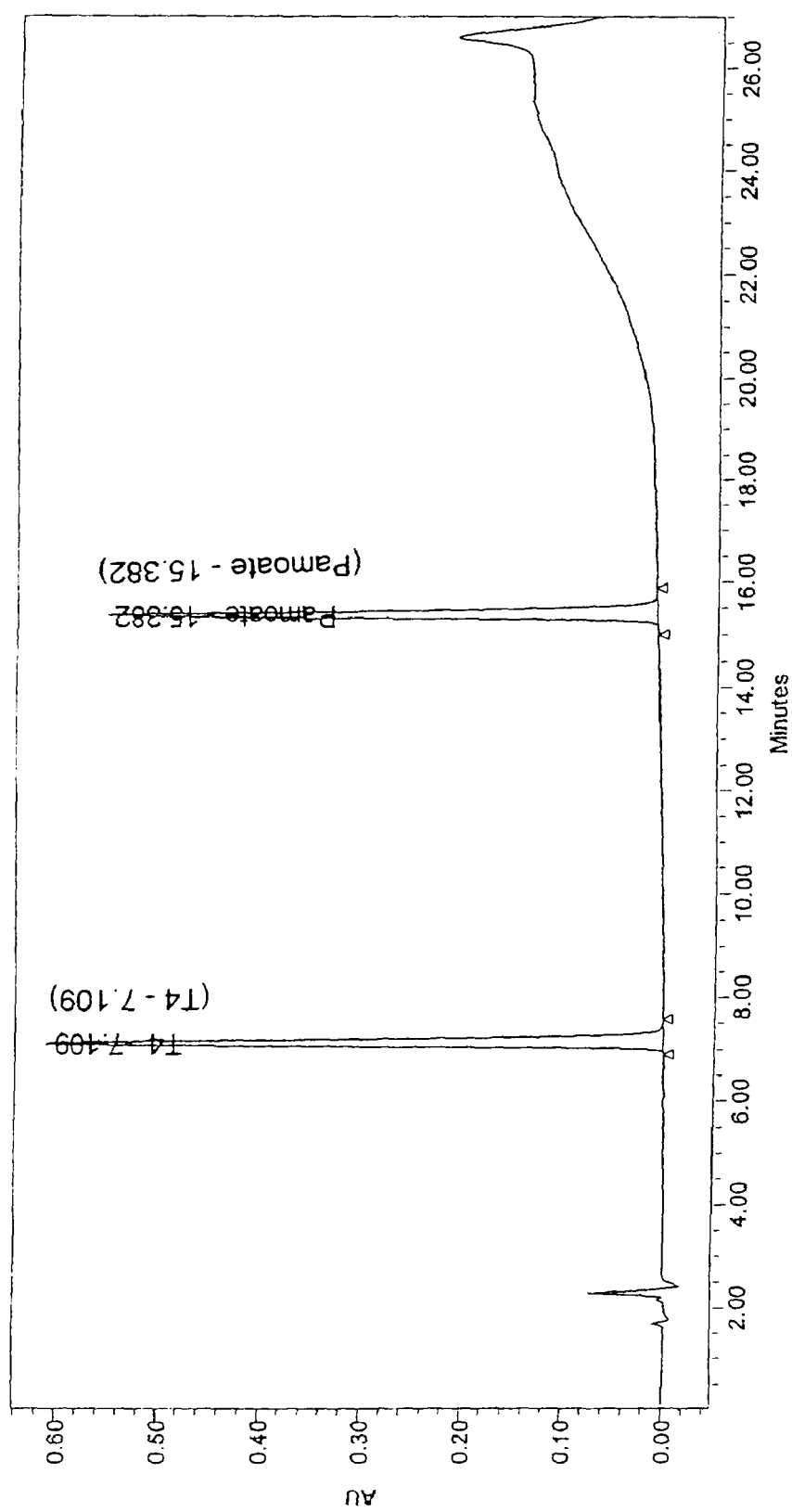
FIG. 13 is an HPLC chromatogram of freshly prepared levothyroxine pamoate.

To $T_4$ (51.06 g, 65.7 mmol) in methanol (400.00 g) as a mixture was added 1N HCl (66.0 mL, 66.0 mmol). Additional methanol (455.0 g) was added to the mixture and the mixture was stirred for 20 min to achieve a solution. The solution was filtered (GF/B 55 mm) to clarify and clear the solution. In a separate flask, disodium pamoate (14.82 g, 14.22 dry, 4.2% $H_2O$, 32.9 mmol) in USP water (318.0 g) was stirred at pH 10.41. HCl (0.02N, 3.5 mL) was added to adjust the solution to about pH 9.5 at about 20° C. To the disodium pamoate solution was added dropwise the T4/HCl/CH$_3$OH solution via a metered addition funnel over approximately 2.1 h. Immediate precipitation of tan solids was observed. After complete addition, the mixture was stirred for about 1.2 h. Solids were collected by filtration (2×125 mm Büchner, Qual 4). Solids on both Büchner funnels were washed with USP water (200 g×2) and dried on the Büchner funnels under a $N_2$ blanket for approximately 2.5 h. Yellow solids were transferred to a drying dish and dried under vacuum at 44-48° C. with a $N_2$ sweep (15" Hg). After about 18 h, levothyroxine pamoate (60.38 g, 94.5% wt. yield) was transferred to an amber bottle. The material was characterized by DSC (FIG. 9), FTIR (FIG. 10), PXRD (FIG. 11), $^1$H NMR (FIG. 12) and HPLC (FIG. 13).

Example 3

Chromatographic Procedures

Chromatographic analyses were conducted on a Waters Breeze system equipped with a Waters 1525 Binary HPLC pump, 717plus Autosampler, 2487 Dual I Absorbance Detector and column heater employing a Zorbax Extend-C-18 Column (4.6×250 mm; 5 micron, 80 A). Separation occurred using a linear gradient elution according to the following table wherein eluant A consisted of 0.1% TFA in water and eluant B consisted of 0.1% TFA in acetonitrile.

|   | Time min | % A | % B | Curve |
|---|---|---|---|---|
| 1 |    | 60 | 40 |   |
| 2 | 15 | 40 | 60 | 6 |
| 3 | 20 | 0  | 100 | 6 |
| 4 | 22 | 0  | 100 | 6 |
| 5 | 23 | 60 | 40 | 6 |
| 6 | 27 | 60 | 40 | 6 |

Injection samples were prepared in water/1N NaOH/acetonitrile diluent (59:1:40) with analyte peaks detected at 230 nm. Analyte peaks associated with the pamoate salts were assayed against standard solutions prepared from liothyronine and levothryroxine.

The HPLC methodology was applied to freshly prepared samples of T3-pamoate and T4 pamoate and the resulting chromatograms compared with chromatograms of the materials after a four-year real-time storage under ambient laboratory conditions. Further, the pamoate salts were evaluated under forced degradation conditions to evaluate the effects of heat and moisture on the salts' chemical and thermal stability. Blank injections of the sample diluent were obtained at each time interval to determine if minor response differences observed were attributable to the diluent and the chromatographic system (eluant) or to real impurities within either liothyronine pamoate or levothyroxine pamoate. Representative chromatograms of the blank injections are provided in FIG. 6 and FIG. 8.

Example 4

Chromatographic Comparison of Real-Time Stability Testing versus Forced-Degradation Studies Samples of levothyroxine pamoate and liothyronine pamoate were stored under ambient laboratory conditions for about four (4) years in amber glass jars. The ambient conditions were defined as room temperatures moderated by HVAC to maintain temperatures of 18-25° C. The samples were exposed to normal fluorescent lighting for up to fifteen (15) hours per day and rarely exposed to daylight.

Figure 6:
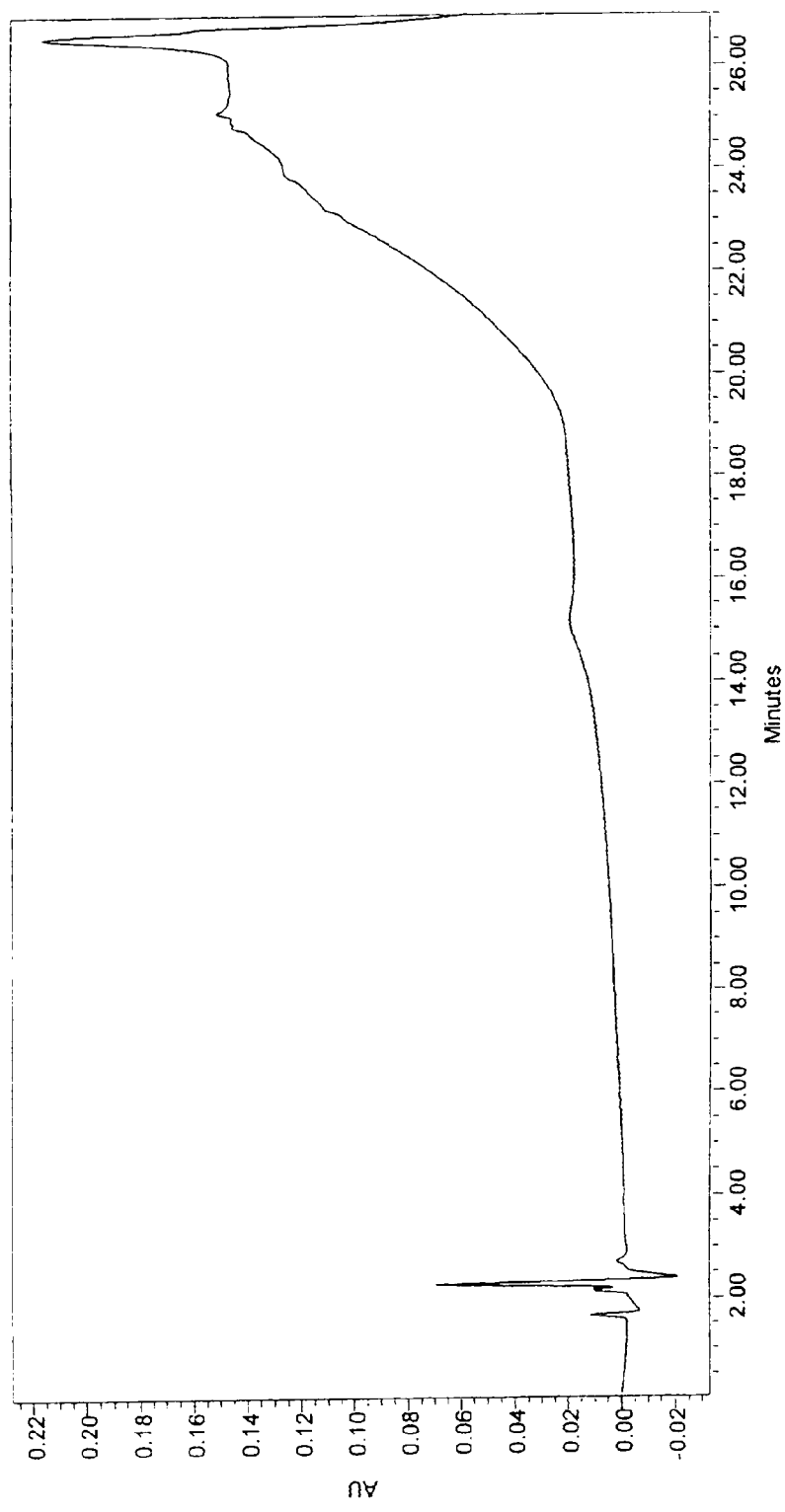
FIG. 6 is an HPLC chromatogram of the eluant used in the chromatographic procedure.
Figure 7:
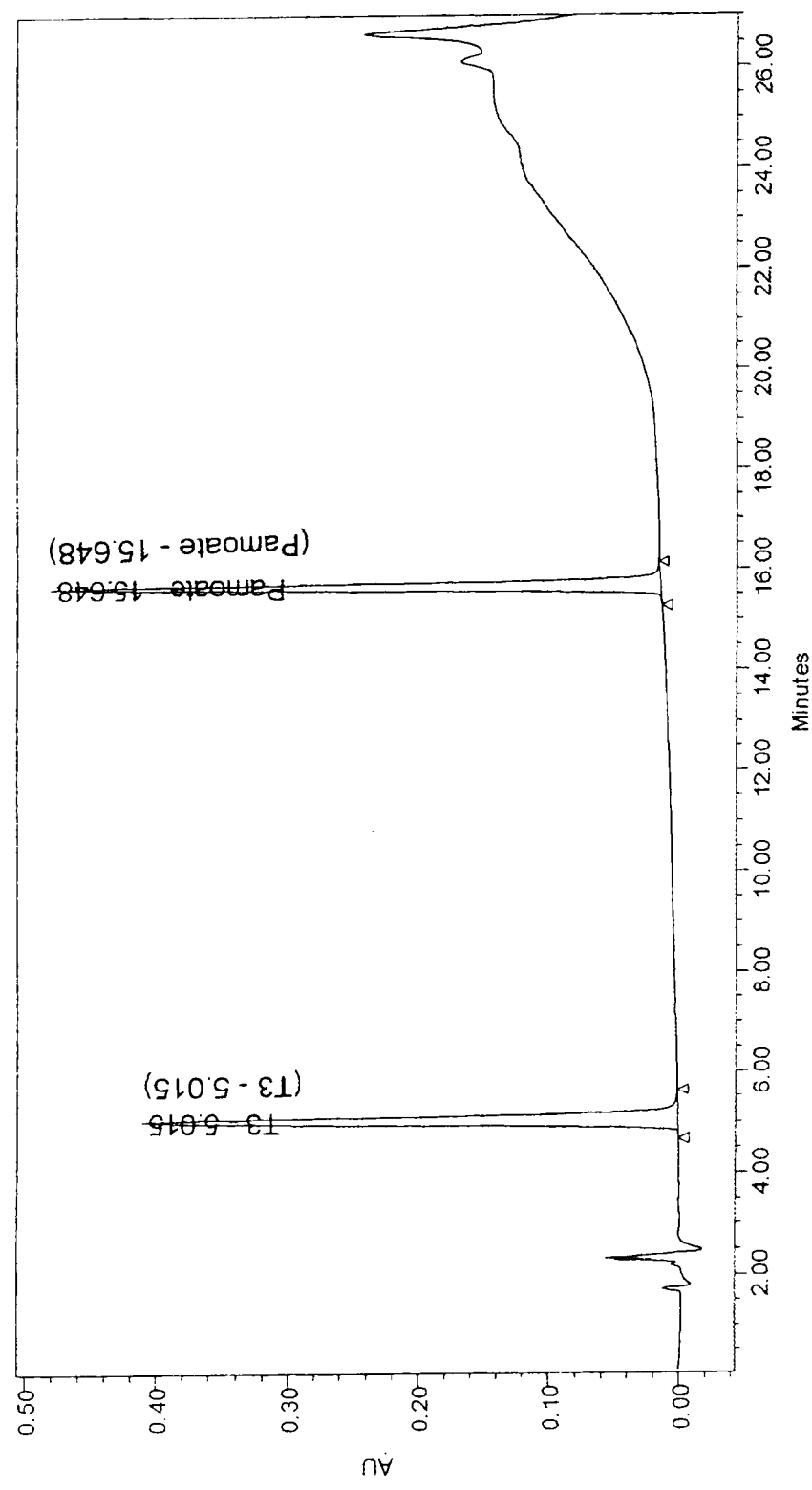
FIG. 7 is an HPLC chromatogram of liothyronine pamoate after extended storage at room temperature.
Figure 8:
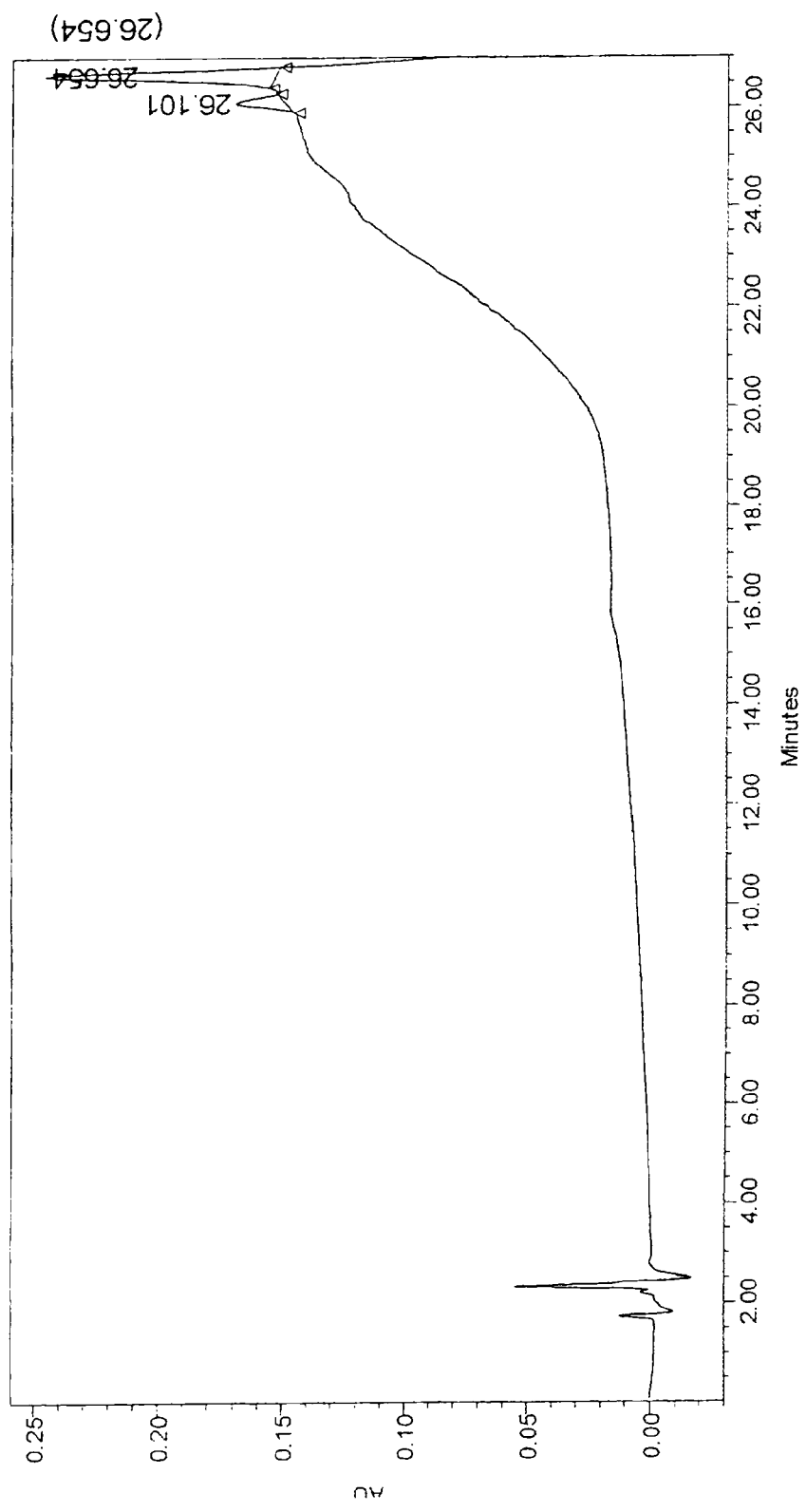
FIG. 8 is an HPLC chromatogram of the eluant used in the chromatographic procedure at a second analysis period.
Figure 14:
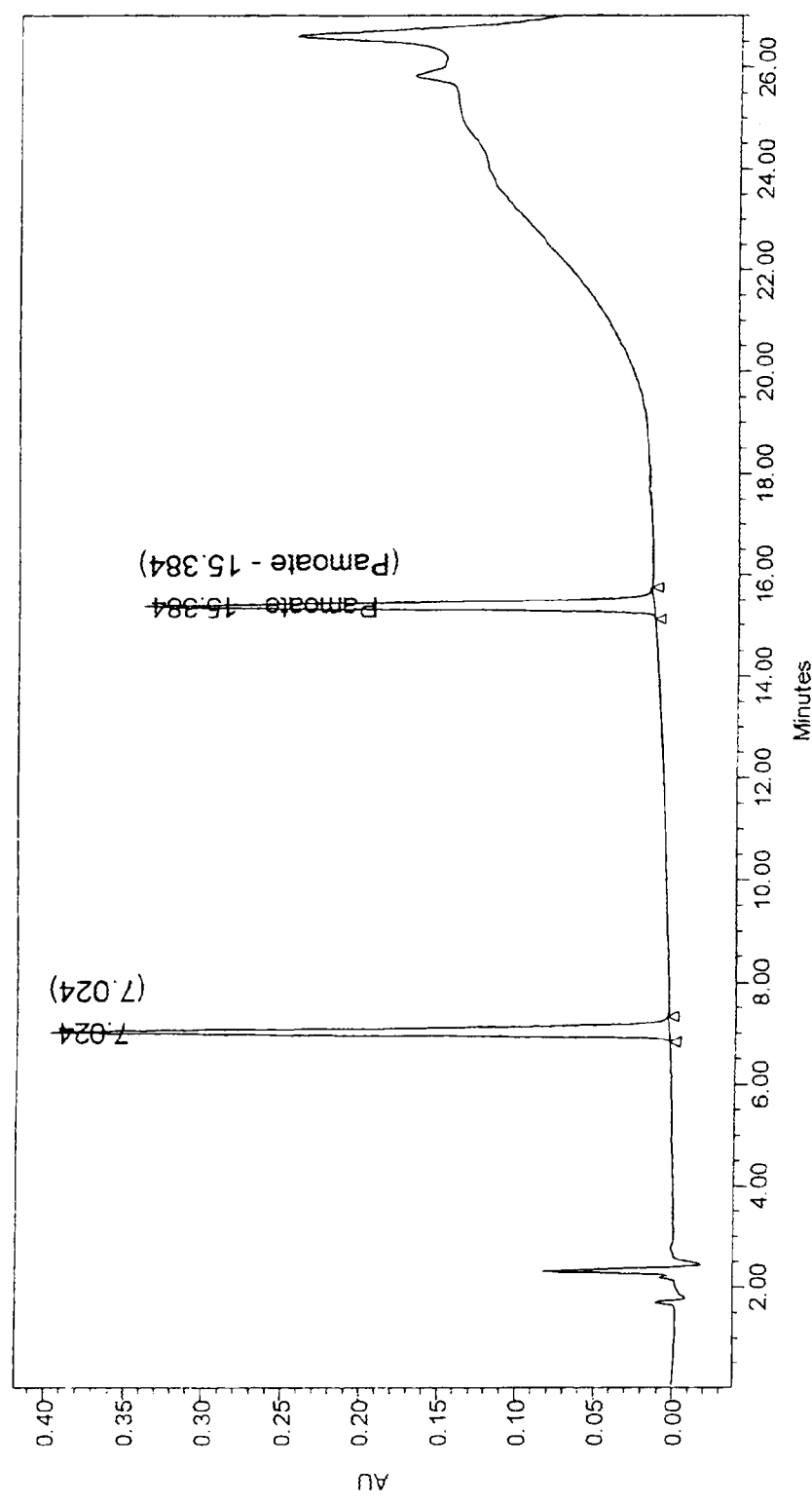
FIG. 14 is an HPLC chromatogram of levothyroxine pamoate after extended storage conditions at room temperature.
Figure 16:
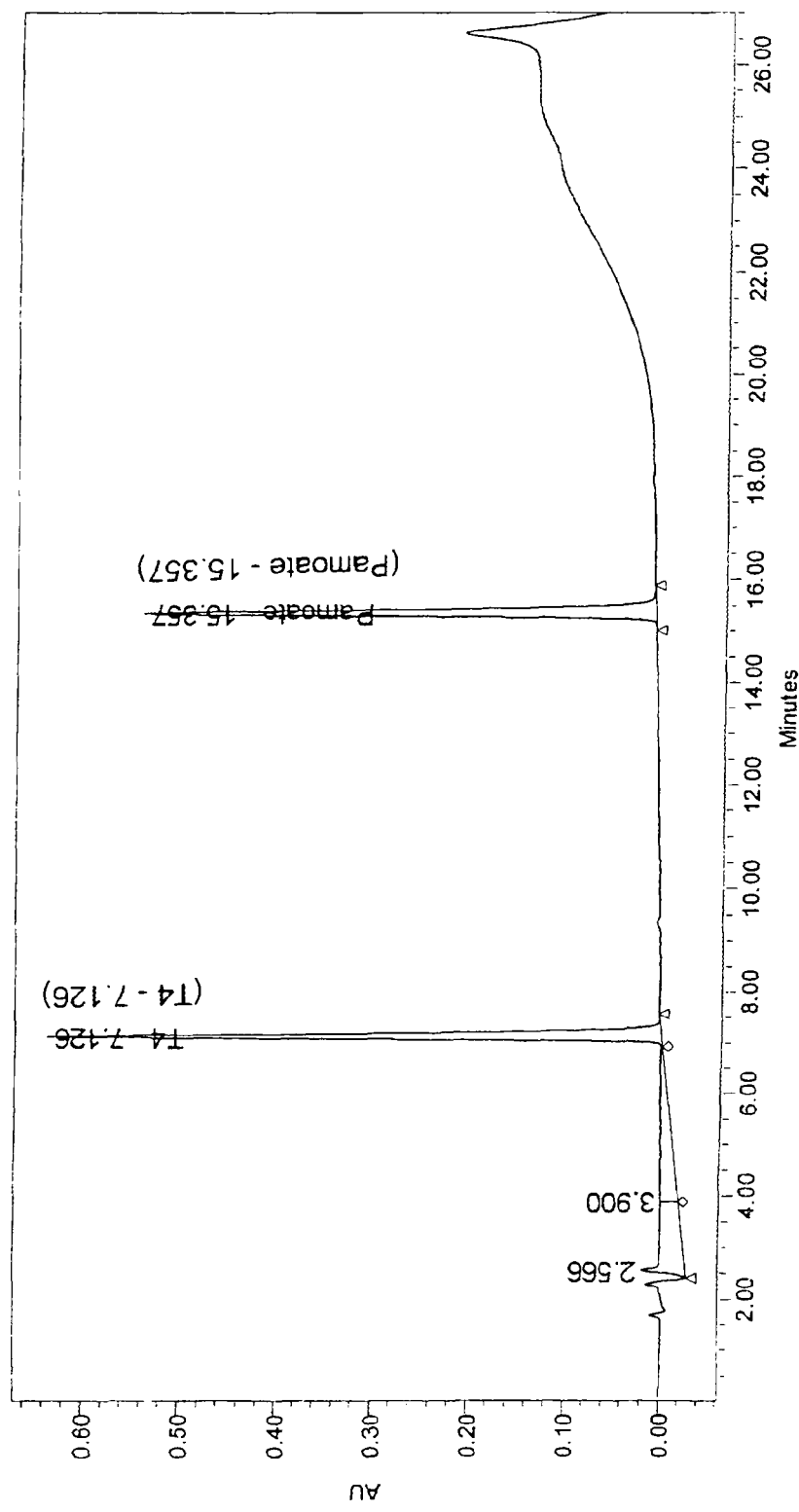
FIG. 16 is an HPLC chromatogram of levothyroxine pamoate after subjection to forced degradation conditions.

To accelerate the potential degradation of levothyroxine pamoate and liothyronine pamoate, samples of each were individually placed in at least an 100 fold excess by weight USP water to form a suspension. The mixture was not degassed and heating was initiated to about 60° C. Multiple samples at each time point were obtained and analyzed from the mixture to assure a representative sample was obtained. FIG. 16 is an HPLC chromatogram of levothyroxine pamoate after subjection to this forced degradation condition for about 98 hours and is indicative of the unexpected stability associated with the organic acid addition salt. Indeed, The results contained within FIG. 16 are essentially identical to those obtained for freshly prepared levothyroxine pamoate (FIG. 13), and for material stored for approximately 4 years (FIG. 14). FIGS. 6 and 8 are representative of the eluant responses (i.e. blank injections) at the time-zero and four year periods.

Figure 15:
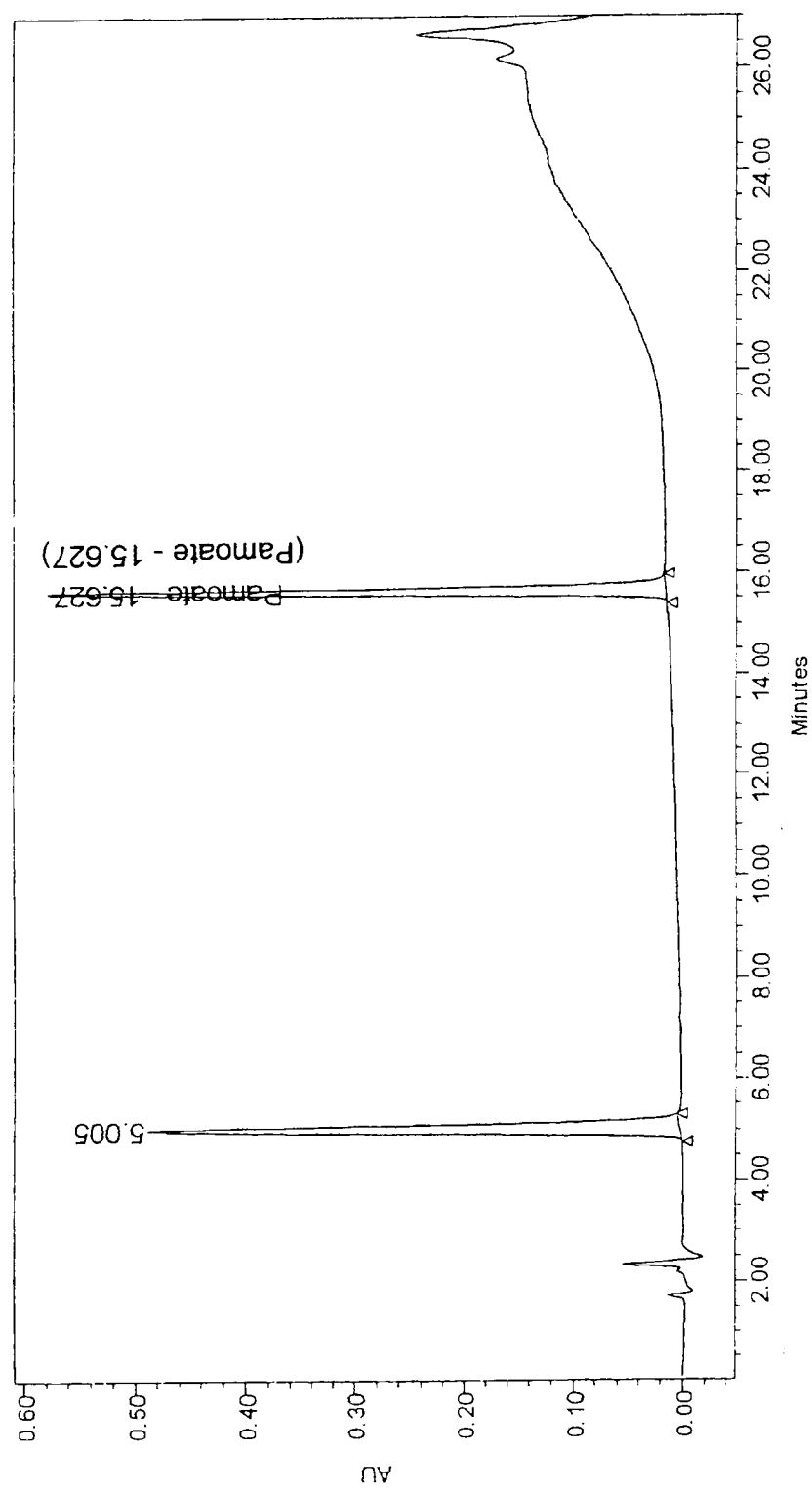
FIG. 15 is an HPLC chromatogram of liothyronine pamoate after extended storage conditions at room temperature.
Figure 17:
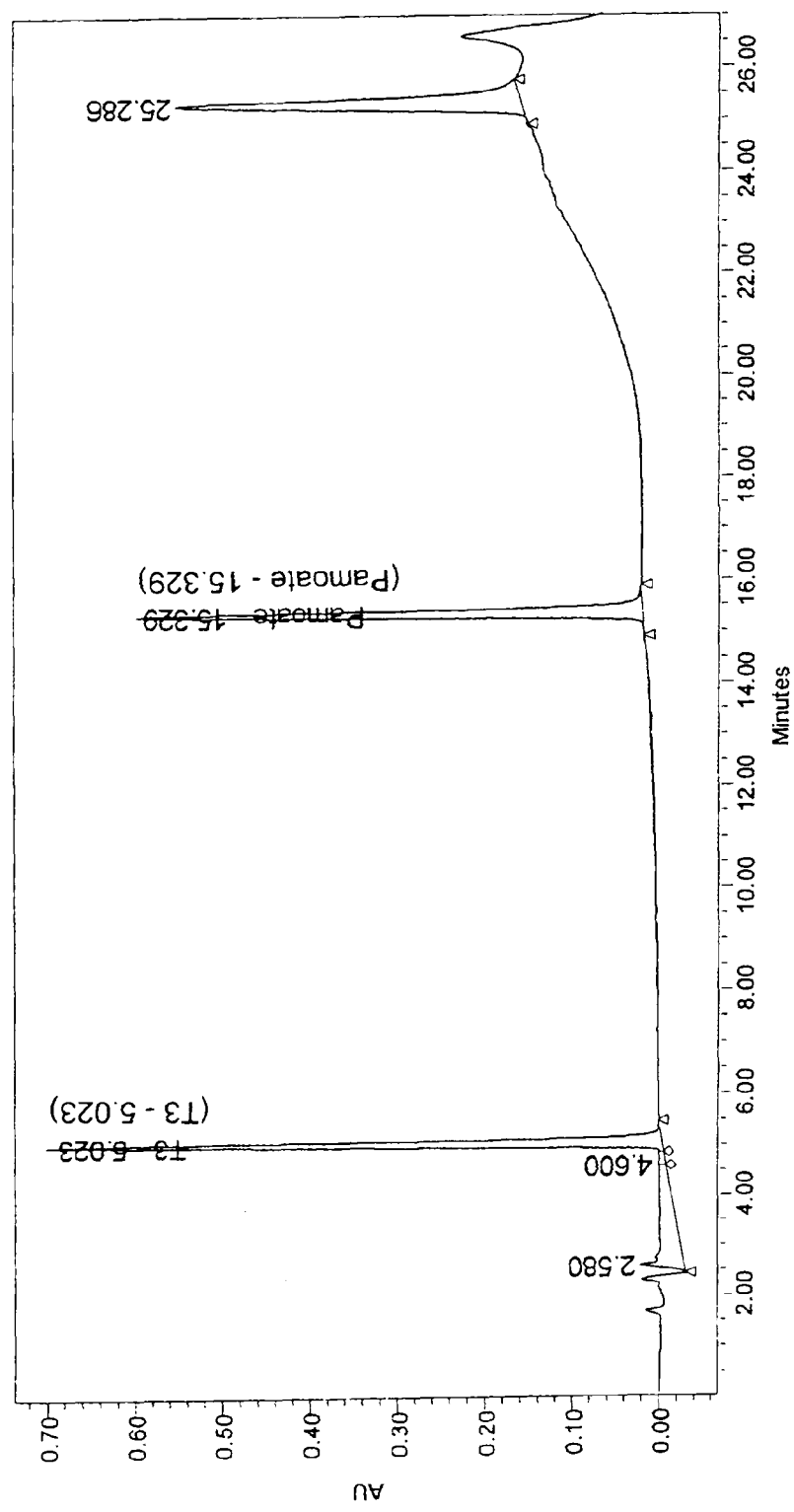
FIG. 17 is an HPLC chromatogram of liothyronine pamoate after subjection to forced degradation conditions.

FIG. 17 is an HPLC chromatogram of liothyronine pamoate after subjection to the forced degradation in an aqueous environment at 60° C. for 148 hours. Under these condition liothyronine pamoate exhibited some decomposition as observed by a late eluting peak with a retention time of about 25-26 minutes. It is beneficial to compare the HPLC results obtained for freshly prepared, extended storage and forced degradation samples of liothyronine pamoate (FIGS. 5, 15 and 17, respectively) with the blank injection chromatograms (FIGS. 6 and 8) to assure the degradation impurity is not related to the minor peak observed at a retention time of 26 minutes. Indeed, the extended storage condition yielded only a minor amount of the impurity observed at a retention time of 25-26 minutes, while the forced degradation impurity was significant.

Other embodiments and modifications may occur to those of ordinary skill in the art subsequent to a review of the information presented herein; these embodiments and modifications, as well as equivalents thereof, are also included within the scope of this invention.

The recited order of processing elements or sequences, or the use of numbers, letters, or other designations therefore, is not intended to limit a claimed process to any order except as specified in the claim itself.

The invention claimed is:

1. A pharmaceutical composition comprising the salt of a thyroid hormone selected from the group consisting of levothyroxine and liothyronine and an organic acid comprising at least one aromatic ring having at least one hydroxyl moiety and at least one carboxylic acid moiety in an ortho relationship.

2. The pharmaceutical composition of claim 1 wherein said organic acid is defined as

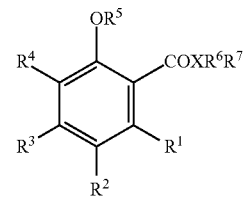

Structure A wherein $R^1$-$R^4$ are independently selected from H, alkyl of 1-6 carbons, adjacent groups may be taken together to form a cyclic alkyl or cyclic aryl moiety; $R^5$ represents H, alkyl, alkylacyl or arylacyl; $R^6$ and $R^7$ are independently selected from H, alkyl of 1-6 carbons, aryl of 6-12 carbons, alkylacyl or arylacyl analogues sufficient to satisfy the valence of X; X is selected from nitrogen, oxygen or sulfur, and when X=O, $R^6$+$R^7$ may represent an alkali earth cation, ammonium or together form a heterocyclic moiety.

3. The pharmaceutical composition of claim 2 wherein said organic acid is defined as

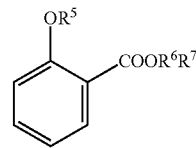

Structure B wherein $R^5$, $R^6$ and $R^7$ remain as defined above for Structure A.

4. The pharmaceutical composition of claim 2 wherein said organic acid is defined as

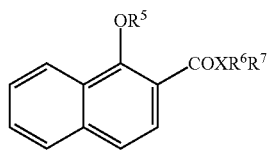

Structure C wherein X, $R^5$, $R^6$ and $R^7$ remain as defined above for Structure A.

5. The pharmaceutical composition of claim 2 wherein said organic acid is defined as

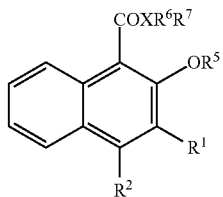

Structure D wherein X, $R^1$, $R^2$, $R^5$, $R^6$ and $R^7$ remain as defined above for Structure A.

6. The pharmaceutical composition of claim 2 wherein said organic acid is defined as

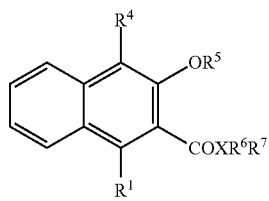

Structure E wherein X, $R^1$, $R^4$, $R^5$, $R^6$ and $R^7$ remain as defined above for Structure A.

7. The pharmaceutical composition of claim 2 wherein said organic acid is defined as

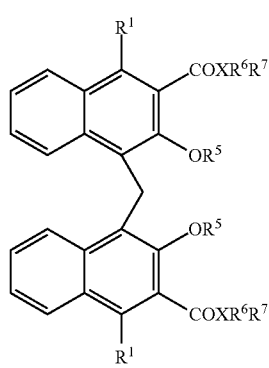

Structure F wherein X, $R^1$, $R^5$, $R^6$ and $R^7$ are independently defined as above for Structure A.

8. The pharmaceutical composition of claim 2 wherein said organic acid is defined as

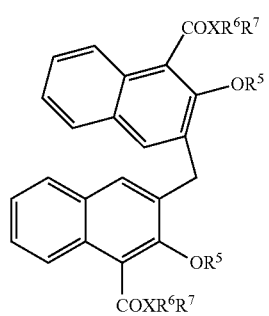

Structure G wherein X, $R^5$, $R^6$ and $R^7$ are independently defined as above for Structure A.

9. The pharmaceutical composition of claim 1 wherein said organic acid is selected from the group consisting of pamoic acid, disodium pamoate, di-ammonium pamoate, di-potassium pamoate, di-alkyl and/or di-aryl amine pamoate, di-alkyl and/or di-aryl esters of pamoic acid, and di-alkylacyl and/or di-arylacyl O-esters of pamoic acid.

10. The pharmaceutical composition of claim 9 wherein said organic acid is selected from the group consisting of pamoic acid and disodium pamoate.

11. The pharmaceutical composition of claim 1 wherein said thyroid hormone and said organic acid are in a stoichiometric ratio of 1:1 to 2:1.

12. The pharmaceutical composition of claim 1 wherein said thyroid hormone and said organic acid are in a stoichiometric ratio of 1:1.

13. The pharmaceutical composition of claim 1 wherein said thyroid hormone and said organic acid are in a stoichiometric ratio of 2:1.

14. The pharmaceutical composition of claim 1 comprising 25-300 μg of said thyroid hormone per unit dose.

15. The pharmaceutical composition of claim 1 in a form selected from a pill, a tablet, a capsule, a solution, a suspension injection dose, a transdermal patch and an inhalation formulation.

16. A drug product comprising said pharmaceutical composition of claim 1.

17. The pharmaceutical composition of claim 1 further comprising at least one additive selected from an excipient, a processing aid and a buffer.

18. The pharmaceutical composition of claim 1 wherein said salt comprises liothyronine pamoate with a differential scanning calorimetry thermogram of FIG. 1.

19. The pharmaceutical composition of claim 1 wherein said salt comprises liothyronine pamoate with a Fourier Transform Infrared spectrum of FIG. 2.

20. The pharmaceutical composition of claim 1 wherein said salt comprises liothyronine pamoate with a Powder X-Ray Diffraction diffractogram of FIG. 3.

21. The pharmaceutical composition of claim 1 wherein said salt comprises liothyronine pamoate with a proton nuclear magnetic resonance spectrum of FIG. 4.

22. The pharmaceutical composition of claim 1 wherein said salt comprises liothyronine pamoate with a high pressure liquid chromatograph chromatogram of FIG. 5.

23. The pharmaceutical composition of claim 1 wherein said comprises levothyroxine pamoate with a differential scanning calorimetry thermogram of FIG. 9.

24. The pharmaceutical composition of claim 1 wherein said salt comprises levothyroxine pamoate with a Fourier Transform Infrared spectrum of FIG. 10.

25. The pharmaceutical composition of claim 1 wherein said salt comprises levothyroxine pamoate with a Powder X-Ray Diffraction diffractogram of FIG. 11.

26. The pharmaceutical composition of claim 1 wherein said salt comprises levothyroxine pamoate with a proton nuclear magnetic resonance spectrum of FIG. 12.

27. The pharmaceutical composition of claim 1 wherein said salt comprises levothyroxine pamoate with an HPLC chromatogram of FIG. 13.

28. The pharmaceutical composition of claim 1 wherein said salt of a thyroid hormone is selected from the group consisting of levothyroxine pamoate and liothyronine pamoate.

29. A method of administering a thyroid hormone comprising:
   forming a drug substance comprising a salt of a thyroid hormone selected from the group consisting of levothyroxine and liothyronine and an organic acid comprising at least one aromatic ring having at least one hydroxyl moiety and at least one carboxylic acid moiety in an ortho relationship;
   incorporating said drug substance into a drug product wherein said drug product has 25-300 μg of said thyroid hormone and a molar ratio of said thyroid hormone to said organic acid of at least 0.9:1 to no more than 2.1:1; and
   administering said drug product to a patient.

30. A method of manufacturing a stable drug substance as a thyroid treatment comprising:
   combining a thyroid hormone with a predetermined first stoichiometric ratio of an organic acid comprising at least one aromatic ring having at least one hydroxyl moiety and at least one carboxylic acid moiety in an ortho relationship thereby forming a thyroid hormone salt;
   storing said thyroid hormone salt for a predetermined time thereby forming an aged drug substance; and
   determining a second stoichiometric ratio of said thyroid hormone and said organic acid in said aged drug substance.

31. A method of manufacturing a drug product as a thyroid treatment comprising:
   combining a thyroid hormone with a predetermined first stoichiometric ratio of organic acid comprising at least one aromatic ring having at least one hydroxyl moiety and at least one carboxylic acid moiety, both in an ortho or vicinal relationship thereby forming a thyroid hormone salt;
   forming a drug product comprising said thyroid hormone salt;
   storing said drug product for a predetermined time thereby forming an aged drug product; and
   determining a second stoichiometric ratio of said thyroid hormone and said organic acid salt in said aged drug product.

32. A process for the preparation of an organic acid salt of a thyroid hormone comprising the steps of:
   a) preparing a first mixture comprising an alkali earth salt, free base or mineral acid salt of said thyroid hormone;
   b) preparing an organic acid mixture wherein said organic acid comprises at least one aromatic ring substituted with at least one hydroxyl group and at least one carboxyl group in an ortho relationship to one another,
   c) combining said first mixture and said organic acid mixture wherein said thyroid hormone and said aromatic acid form said organic acid salt of a thyroid hormone;
   d) isolating said organic acid salt of a thyroid hormone by at least one method selected from filtration, centrifugation and solvent evaporation; and
   e) purifying said organic acid salt of a thyroid hormone by at least one method selected from recrystallization, digestion and chromatographic separation.

33. A process for the preparation of a purified thyroid hormone comprising the steps of:
   obtaining a first mixture comprising at least one thyroid hormone selected from liothyronine and levothyroxine;
   reacting said first mixture with an organic acid wherein said organic acid comprises at least one aromatic ring substituted with at least one hydroxyl group and at least one carboxyl group in an ortho relationship to one another thereby forming an organic acid salt of said thyroid hormone.

34. A pharmaceutical composition comprising the salt of a thyroid hormone selected from the group consisting of levothyroxine and liothyronine and a stoichiometric amount of an organic acid comprising at least one aromatic ring having at least one hydroxyl moiety and at least one carboxylic acid moiety in an ortho relationship wherein said salt is stable for at least one year to variations in at least one of water content, heat, light, oxidative conditions and pH changes as indicated by said stoichiometric amount varying by less than 5% as measured by chromatographic techniques.

35. The method of administering a thyroid hormone of claim 29 wherein said organic acid is defined as

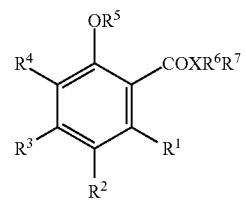

Structure A wherein $R^1$-$R^4$ are independently selected from H, alkyl of 1-6 carbons, adjacent groups may be taken together to form a cyclic alkyl or cyclic aryl moiety; $R^5$ represents H, alkyl, alkylacyl or arylacyl; $R^6$ and $R^7$ are independently selected from H, alkyl of 1-6 carbons, aryl of 6-12 carbons, alkylacyl or arylacyl analogues sufficient to satisfy the valence of X; X is selected from nitrogen, oxygen or sulfur, and when X=O, $R^6$+$R^7$ may represent an alkali earth cation, ammonium or together form a heterocyclic moiety.

36. The method of administering a thyroid hormone of claim 35 wherein said organic acid is defined as

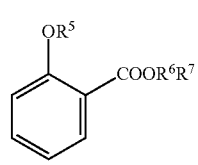

Structure B wherein $R^5$, $R^6$ and $R^7$ remain as defined above for Structure A.

37. The method of administering a thyroid hormone of claim 35 wherein said organic acid is defined as

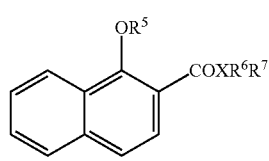

Structure C wherein X, $R^5$, $R^6$ and $R^7$ remain as defined above for Structure A.

38. The method of administering a thyroid hormone of claim 35 wherein said organic acid is defined as

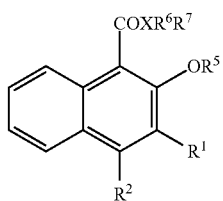

Structure D wherein X, $R^1$, $R^2$, $R^5$, $R^6$ and $R^7$ remain as defined above for Structure A.

39. The method of administering a thyroid hormone of claim 35 wherein said organic acid is defined as

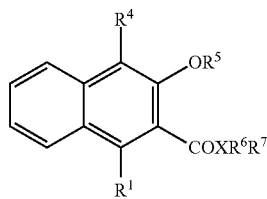

Structure E wherein X, $R^1$, $R^4$, $R^5$, $R^6$ and $R^7$ remain as defined above for Structure A.

40. The method of administering a thyroid hormone of claim 35 wherein said organic acid is defined as

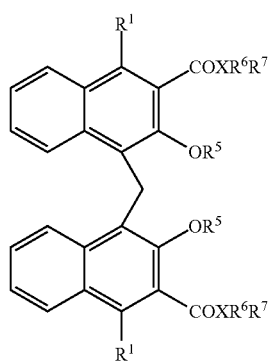

Structure F wherein X, $R^1$, $R^5$, $R^6$ and $R^7$ are independently defined as above for Structure A.

41. The method of administering a thyroid hormone of claim 35 wherein said organic acid is defined as

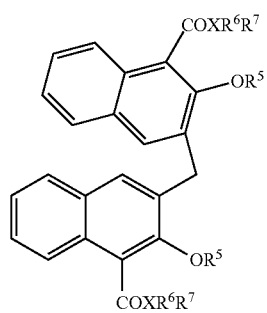

Structure G wherein X, $R^5$, $R^6$ and $R^7$ are independently defined as above for Structure A.

42. The method of administering a thyroid hormone of claim 29 wherein said organic acid is selected from the group consisting of pamoic acid, disodium pamoate, di-ammonium pamoate, di-potassium pamoate, di-alkyl and/or di-aryl amine pamoate, di-alkyl and/or di-aryl esters of pamoic acid, and di-alkylacyl and/or di-arylacyl O-esters of pamoic acid.

43. The method of administering a thyroid hormone of claim 42 wherein said organic acid is selected from the group consisting of pamoic acid and disodium pamoate.

44. The method of administering a thyroid hormone of claim 29 wherein said drug product is an oral dose.

45. The method of administering a thyroid hormone of claim 29 wherein said drug product is in a form selected from a pill, a tablet, a capsule a solution, a suspension injection dose, a transdermal patch and an inhalation formulation.

46. The method of administering a thyroid hormone of claim 29 wherein said drug product further comprises at least one additive selected from an excipient, a processing aid and a buffer.

47. The method of administering a thyroid hormone of claim 29 wherein said salt of a thyroid hormone is selected from the group consisting of levothyroxine pamoate and liothyronine pamoate.

48. The method of administering a thyroid hormone of claim 29 wherein said thyroid hormone is administered for treatment of at least one disease selected from hypothyroidism; cretinism, myxedema, nontoxic goiter, nonendemic goiter, chronic lymphocytic thyroiditis, and thyroid cancer.

49. The method of manufacturing a stable drug substance of claim 30 comprising determining said second stoichiometric ratio by a chromatographic technique.

50. The method of manufacturing a stable drug substance of claim 30 wherein said predetermined time is at least 1 year.

51. The method of manufacturing a stable drug substance of claim 30 wherein said predetermined time is at least 2 years.

52. The method of manufacturing a stable drug substance of claim 51 wherein said predetermined time is at least 4 years.

53. The method of manufacturing a stable drug substance of claim 30 wherein said storing is under accelerated aging conditions comprising at least one perturbation from ambient selected from temperature above ambient, temperature below ambient, light exposure, solvent exposure, pH alterations, oxidative conditions and exposure to an atmosphere which differs from air.

54. The method of manufacturing a stable drug substance of claim 53 wherein said storing is at ambient conditions.

55. The method of manufacturing a stable drug substance of claim 54 wherein said second stoichiometric ratio is at least 95% to no more than 105% of said first stoichiometric ratio.

56. The method of manufacturing a stable drug substance of claim 55 wherein said second stoichiometric ratio is at least 98% to no more than 102% of said first stoichiometric ratio.

57. The method of manufacturing a stable drug substance of claim 56 wherein said second stoichiometric ratio is at least 99% to no more than 101% of said first stoichiometric ratio.

58. The method of manufacturing a stable drug substance of claim 30 wherein said drug product is a solid oral dose.

59. The method of manufacturing a stable drug substance of claim 30 wherein said organic acid is defined as

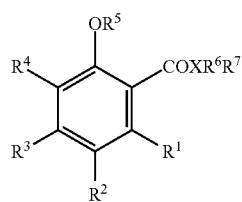

Structure A wherein R¹-R⁴ are independently selected from H, alkyl of 1-6 carbons, adjacent groups may be taken together to form a cyclic alkyl or cyclic aryl moiety; R⁵ represents H, alkyl, alkylacyl or arylacyl; R⁶ and R⁷ are independently selected from H, alkyl of 1-6 carbons, aryl of 6-12 carbons, alkylacyl or arylacyl analogues sufficient to satisfy the valence of X; X is selected from nitrogen, oxygen or sulfur, and when X=O, R⁶+R⁷ may represent an alkali earth cation, ammonium or together form a heterocyclic moiety.

60. The method of manufacturing a stable drug substance of claim 59 wherein said organic acid is defined as

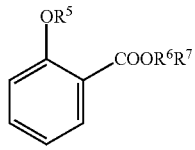

Structure B wherein R⁵, R⁶ and R⁷ remain as defined above for Structure A.

61. The method of manufacturing a stable drug substance of claim 59 wherein said organic acid is defined as

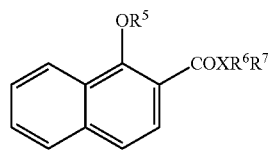

Structure C wherein X, R⁵, R⁶ and R⁷ remain as defined above for Structure A.

62. The method of manufacturing a stable drug substance of claim 59 wherein said organic acid is defined as

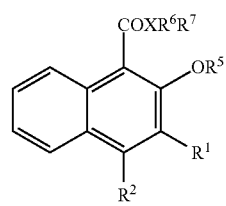

Structure D wherein X, R¹, R², R⁵, R⁶ and R⁷ remain as defined above for Structure A.

63. The method of manufacturing a stable drug substance of claim 59 wherein said organic acid is defined as

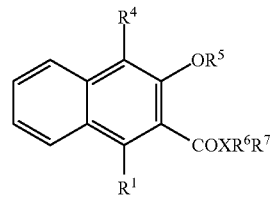

Structure E wherein X, R¹, R⁴, R⁵, R⁶ and R⁷ remain as defined above for Structure A.

64. The method of manufacturing a stable drug substance of claim 59 wherein said organic acid is defined as

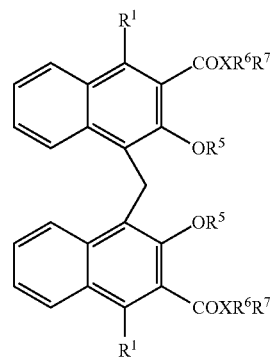

Structure F wherein X, R¹, R⁵, R⁶ and R⁷ are independently defined as above for Structure A.

65. The method of manufacturing a stable drug substance of claim 59 wherein said organic acid is defined as

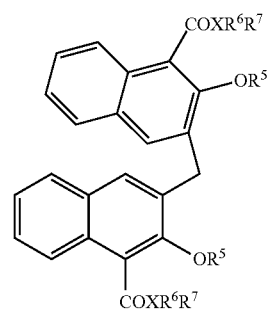

Structure G wherein X, R⁵, R⁶ and R⁷ are independently defined as above for Structure A.

66. The method of manufacturing a stable drug substance of claim 30 wherein said organic acid is selected from the group consisting of pamoic acid, disodium pamoate, di-ammonium pamoate, di-potassium pamoate, di-alkyl and/or di-aryl amine pamoate, di-alkyl and/or di-aryl esters of pamoic acid, and di-alkylacyl and/or di-arylacyl O-esters of pamoic acid.

67. The method of manufacturing a stable drug substance of claim 66 wherein said organic acid salt is selected from the group consisting of pamoic acid and disodium pamoate.

68. The method of manufacturing a stable drug substance of claim 30 wherein said thyroid hormone and said organic acid are in a stoichiometric ratio of 1:1 to 2:1.

69. The method of manufacturing a stable drug substance of claim 30 wherein said thyroid hormone and said organic acid are in a stoichiometric ratio of 1:1.

70. The method of manufacturing a stable drug substance of claim 30 wherein said thyroid hormone and said organic acid are in a stoichiometric ratio of 2:1.

71. The method of manufacturing a stable drug substance of claim 30 wherein said drug substance comprises 25-300 μg of said thyroid hormone.

72. The method of manufacturing a stable drug substance of claim 30 wherein said drug substance is incorporated into a drug product in a form selected from a pill, a tablet, a capsule, a solution, a suspension injection dose, a transdermal patch and an inhalation formulation.

73. The method of manufacturing a stable drug substance of claim 30 further comprising adding at least one additive selected from an excipient, a processing aid and a buffer.

74. The method of manufacturing a stable drug substance of claim 30 wherein said salt comprises liothyronine pamoate with a differential scanning calorimetry thermogram of FIG. 1.

75. The method of manufacturing a stable drug substance of claim 30 wherein said salt comprises liothyronine pamoate with a Fourier Transform Infrared spectrum of FIG. 2.

76. The method of manufacturing a stable drug substance of claim 30 wherein said salt comprises liothyronine pamoate with a Powder X-Ray Diffraction diffractogram of FIG. 3.

77. The method of manufacturing a stable drug substance of claim 30 wherein said salt comprises liothyronine pamoate with a proton nuclear magnetic resonance spectrum of FIG. 4.

78. The method of manufacturing a stable drug substance of claim 30 wherein said salt comprises liothyronine pamoate with a high pressure liquid chromatograph chromatogram of FIG. 5.

79. The method of manufacturing a stable drug substance of claim 30 wherein said comprises levothyroxine pamoate with a differential scanning calorimetry thermogram of FIG. 9.

80. The method of manufacturing a stable drug substance of claim 30 wherein said salt comprises levothyroxine pamoate with a Fourier Transform Infrared spectrum of FIG. 10.

81. The method of manufacturing a stable drug substance of claim 30 wherein said salt comprises levothyroxine pamoate with a Powder X-Ray Diffraction diffractogram of FIG. 11.

82. The method of manufacturing a stable drug substance of claim 30 wherein said salt comprises levothyroxine pamoate with a proton nuclear magnetic resonance spectrum of FIG. 12.

83. The method of manufacturing a stable drug substance of claim 30 wherein said salt comprises levothyroxine pamoate with an HPLC chromatogram of FIG. 13.

84. The method of manufacturing a stable drug substance of claim 30 wherein said salt of a thyroid hormone is selected from the group consisting of levothyroxine pamoate and liothyronine pamoate.

85. The method of manufacturing a drug product of claim 31 wherein said predetermined time is at least 1 year.

86. The method of manufacturing a drug product of claim 85 wherein said predetermined time is at least 2 years.

87. The method of manufacturing a drug product of claim 86 wherein said predetermined time is 4 years.

88. The method of manufacturing a drug product of claim 31 wherein said storing is under accelerated aging conditions comprising at least one perturbation from ambient selected from temperature above ambient, temperature below ambient, light exposure, solvent exposure, pH alterations, oxidative conditions and exposure to an atmosphere which differs from air.

89. The method of manufacturing a drug product of claim 85 wherein said storing is at ambient conditions.

90. The method of manufacturing a drug product of claim 89 wherein said second stoichiometric ratio is at least 95% to no more than 105% of said first stoichiometric ratio.

91. The method of manufacturing a drug product of claim 90 wherein said second stoichiometric ratio is at least 98% to no more than 102% of said first stoichiometric ratio.

92. The method of manufacturing a drug product of claim 91 wherein said second stoichiometric ratio is at least 99% to no more than 101% of said first stoichiometric ratio.

93. The method of manufacturing a drug product of claim 31 wherein said drug product is a solid oral dose.

94. The method of manufacturing a drug product of claim 31 wherein said organic acid is defined as

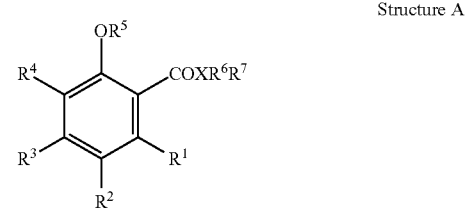

Structure A wherein $R^1$-$R^4$ are independently selected from H, alkyl of 1-6 carbons, adjacent groups may be taken together to form a cyclic alkyl or cyclic aryl moiety; $R^5$ represents H, alkyl, alkylacyl or arylacyl; $R^6$ and $R^7$ are independently selected from H, alkyl of 1-6 carbons, aryl of 6-12 carbons, alkylacyl or arylacyl analogues sufficient to satisfy the valence of X; X is selected from nitrogen, oxygen or sulfur, and when X=O, $R^6$+$R^7$ may represent an alkali earth cation, ammonium or together form a heterocyclic moiety.

95. The method of manufacturing a drug product of claim 94 wherein said organic acid is defined as

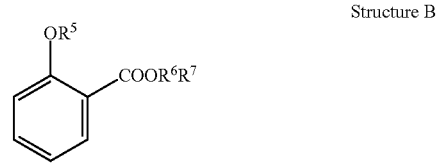

Structure B wherein $R^5$, $R^6$ and $R^7$ remain as defined above for Structure A.

96. The method of manufacturing a drug product of claim 94 wherein said organic acid is defined as

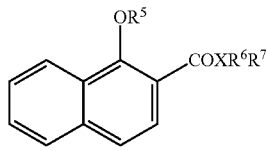

Structure C wherein X, $R^5$, $R^6$ and $R^7$ remain as defined above for Structure A.

97. The method of manufacturing a drug product of claim 94 wherein said organic acid is defined as

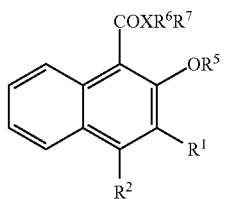

Structure D wherein X, $R^1$, $R^2$, $R^5$, $R^6$ and $R^7$ remain as defined above for Structure A.

98. The method of manufacturing a drug product of claim 94 wherein said organic acid is defined as

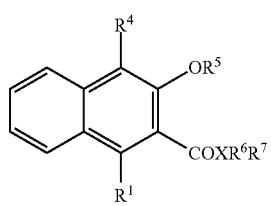

Structure E wherein X, $R^1$, $R^4$, $R^5$, $R^6$ and $R^7$ remain as defined above for Structure A.

99. The method of manufacturing a drug product of claim 94 wherein said organic acid is defined as

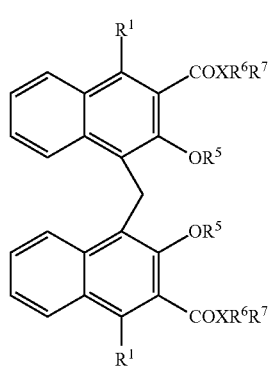

Structure F wherein X, $R^1$, $R^5$, $R^6$ and $R^7$ are independently defined as above for Structure A.

100. The method of manufacturing a drug product of claim 94 wherein said organic acid is defined as

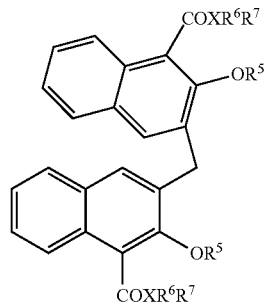

Structure G wherein X, $R^5$, $R^6$ and $R^7$ are independently defined as above for Structure A.

101. The method of manufacturing a drug product of claim 31 wherein said organic acid is selected from the group consisting of pamoic acid, disodium pamoate, di-ammonium pamoate, di-potassium pamoate, di-alkyl and/or di-aryl amine pamoate, di-alkyl and/or di-aryl esters of pamoic acid, and Idi-alkylacyl and/or di-arylacyl O-esters of pamoic acid.

102. The method of manufacturing a drug product of claim 31 wherein said organic acid salt is selected from the group consisting of pamoic acid and disodium pamoate.

103. The method of manufacturing a drug product of claim 31 wherein said thyroid hormone salt and said organic acid are in a stoichiometric ratio of 1:1 to 2:1.

104. The method of manufacturing a drug product of claim 31 wherein said thyroid hormone and said organic acid are in a stoichiometric ratio of 1:1.

105. The method of manufacturing a drug product of claim 31 wherein said thyroid hormone and said organic acid are in a stoichiometric ratio of 2:1.

106. The method of manufacturing a drug product of claim 31 wherein said organic acid salt comprising 25-300 µg of said thyroid hormone.

107. The method of manufacturing a drug product of claim 31 wherein said drug substance is incorporated into a drug product in a form selected from a pill, a tablet, a capsule, a solution, a suspension injection dose, a transdermal patch and an inhalation formulation.

108. The method of manufacturing a drug product of claim 31 further comprising adding at least one additive selected from an excipient, a processing aid and a buffer.

109. The method of manufacturing a drug product of claim 31 wherein said salt comprises liothyronine pamoate with a differential scanning calorimetry thermogram of FIG. 1.

110. The method of manufacturing a drug product of claim 31 wherein said salt comprises liothyronine pamoate with a Fourier Transform Infrared spectrum of FIG. 2.

111. The method of manufacturing a drug product of claim 31 wherein said salt comprises liothyronine pamoate with a Powder X-Ray Diffraction diffractogram of FIG. 3.

112. The method of manufacturing a drug product of claim 31 wherein said salt comprises liothyronine pamoate with a proton nuclear magnetic resonance spectrum of FIG. 4.

113. The method of manufacturing a drug product of claim 31 wherein said salt comprises liothyronine pamoate with a high pressure liquid chromatograph chromatogram of FIG. 5.

114. The method of manufacturing a drug product of claim 31 wherein said salt comprises levothyroxine pamoate with a differential scanning calorimetry thermogram of FIG. 9.

115. The method of manufacturing a drug product of claim 31 wherein said salt comprises levothyroxine pamoate with a Fourier Transform Infrared spectrum of FIG. 10.

116. The method of manufacturing a drug product of claim 31 wherein said salt comprises levothyroxine pamoate with a Powder X-Ray Diffraction diffractogram of FIG. 11.

117. The method of manufacturing a drug product of claim 31 wherein said salt comprises levothyroxine pamoate with a proton nuclear magnetic resonance spectrum of FIG. 12.

118. The method of manufacturing a drug product of claim 31 wherein said salt comprises levothyroxine pamoate with an HPLC chromatogram of FIG. 13.

119. The method of manufacturing a drug product of claim 31 wherein said salt of a thyroid hormone is selected from the group consisting of levothyroxine pamoate and liothyronine pamoate.

120. The process for the preparation of an organic acid salt of a thyroid hormone of claim 32 wherein said thyroid hormone is selected from the group consisting of levothyroxine and liothyronine.

121. The process for the preparation of an organic acid salt of a thyroid hormone of claim 32 wherein said organic acid is defined as

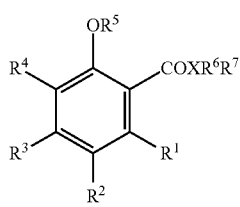

Structure A wherein $R^1$-$R^4$ are independently selected from H, alkyl of 1-6 carbons, adjacent groups may be taken together to form a cyclic alkyl or cyclic aryl moiety; $R^5$ represents H, alkyl, alkylacyl or arylacyl; $R^6$ and $R^7$ are independently selected from H, alkyl of 1-6 carbons, aryl of 6-12 carbons, alkylacyl or arylacyl analogues sufficient to satisfy the valence of X; X is selected from nitrogen, oxygen or sulfur, and when X=O, $R^6$+$R^7$ may represent an alkali earth cation, ammonium or together form a heterocyclic moiety.

122. The process for the preparation of an organic acid salt of a thyroid hormone of claim 121 wherein said organic acid is defined as

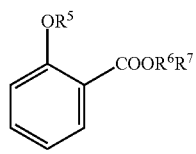

Structure B wherein $R^5$, $R^6$ and $R^7$ remain as defined above for Structure A.

123. The process for the preparation of an organic acid salt of a thyroid hormone of claim 121 wherein said organic acid is defined as

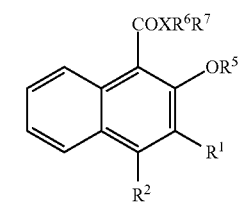

Structure C wherein X, $R^5$, $R^6$ and $R^7$ remain as defined above for Structure A.

124. The process for the preparation of an organic acid salt of a thyroid hormone of claim 121 wherein said organic acid is defined as

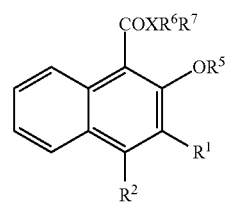

Structure D wherein X, $R^1$, $R^2$, $R^5$, $R^6$ and $R^7$ remain as defined above for Structure A.

125. The process for the preparation of an organic acid salt of a thyroid hormone of claim 121 wherein said organic acid is defined as

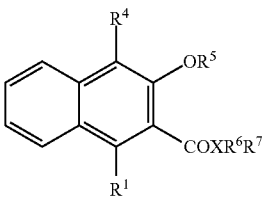

Structure E wherein X, $R^1$, $R^4$, $R^5$, $R^6$ and $R^7$ remain as defined above for Structure A.

126. The process for the preparation of an organic acid salt of a thyroid hormone of claim 121 wherein said organic acid is defined as

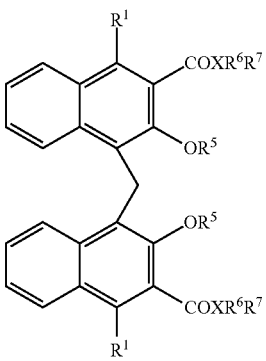

Structure F wherein X, $R^1$, $R^5$, $R^6$ and $R^7$ are independently defined as above for Structure A.

127. The process for the preparation of an organic acid salt of a thyroid hormone of claim 121 wherein said organic acid is defined as

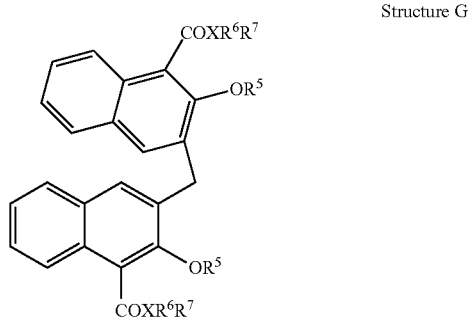

Structure G wherein X, $R^5$, $R^6$ and $R^7$ are independently defined as above for Structure A.

128. The process for the preparation of an organic acid salt of a thyroid hormone of claim 32 wherein said organic acid is selected from the group consisting of pamoic acid, disodium pamoate, di-ammonium pamoate, di-potassium pamoate, di-alkyl and/or di-aryl amine pamoate, di-alkyl and/or di-aryl esters of pamoic acid, and di-alkylacyl and/or di-arylacyl O-esters of pamoic acid, i.e. those alkylacyl and arylacyl esters formed using the hydroxyl moiety of pamoic acid and not the carboxylic acid functional group.

129. The process for the preparation of an organic acid salt of a thyroid hormone of claim 32 wherein said organic acid is selected from the group consisting of pamoic acid and disodium pamoate.

130. The process for the preparation of an organic acid salt of a thyroid hormone of claim 32 wherein at least one of said first solution and said organic acid solution comprises water.

131. The process for the preparation of an organic acid salt of a thyroid hormone of claim 130 wherein at least one of said first solution and said organic acid solution is at a pH between 1.5 and 13.

132. The process for the preparation of an organic acid salt of a thyroid hormone of claim 32 wherein said thyroid hormone and said organic acid are in a stoichiometric ratio of at least 0.9:1 to no more than 2.1:1.

133. The process for the preparation of an organic acid salt of a thyroid hormone of claim 32 wherein said organic acid salt of a thyroid hormone is selected from the group consisting of levothyroxine pamoate and liothyronine pamoate.

134. The process for the preparation of an organic acid salt of a thyroid hormone of claim 32 wherein said alkali earth salt of said thyroid hormone is selected from sodium liothyronine and sodium levothyroxine.

135. The process for the preparation of an organic acid salt of a thyroid hormone of claim 32 further comprising isolating a polymorph of said organic acid salt of a thyroid hormone.

136. The process for the preparation of an organic acid salt of a thyroid hormone of claim 32 wherein at least one of said first mixture and said organic acid mixture is a liquid.

137. The process for the preparation of an organic acid salt of a thyroid hormone of claim 32 wherein at least one of said first mixture and said organic acid mixture is a solid.

138. The process for the preparation of a purified thyroid hormone of claim 33 further comprising isolating said organic acid salt of said thyroid hormone.

139. The process for the preparation of a purified thyroid hormone of claim 33 wherein said first mixture is a liquid.

140. The process for the preparation of a purified thyroid hormone of claim 33 wherein said first mixture is a solid.

141. The pharmaceutical composition of claim 34 wherein said organic acid is defined as

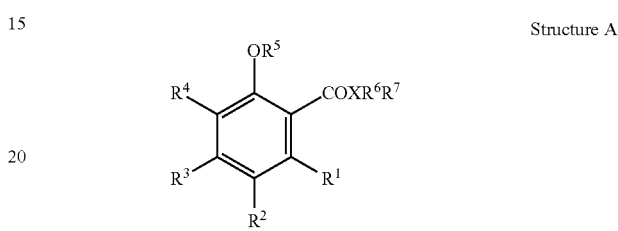

Structure A wherein $R^1$-$R^4$ are independently selected from H, alkyl of 1-6 carbons, adjacent groups may be taken together to form a cyclic alkyl or cyclic aryl moiety; $R^5$ represents H, alkyl, alkylacyl or arylacyl; $R^6$ and $R^7$ are independently selected from H, alkyl of 1-6 carbons, aryl of 6-12 carbons, alkylacyl or arylacyl analogues sufficient to satisfy the valence of X; X is selected from nitrogen, oxygen or sulfur, and when X=O, $R^6$+$R^7$ may represent an alkali earth cation, ammonium or together form a heterocyclic moiety.

142. The pharmaceutical composition of claim 141 wherein said organic acid is defined as

Structure B wherein $R^5$, $R^6$ and $R^7$ remain as defined above for. Structure A.

143. The pharmaceutical composition of claim 141 wherein said organic acid is defined as

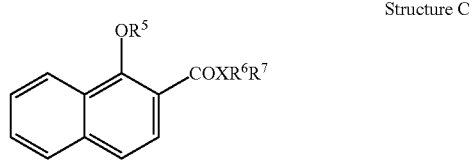

Structure C wherein X, $R^5$, $R^6$ and $R^7$ remain as defined above for Structure A.

144. The pharmaceutical composition of claim 141 wherein said organic acid is defined as

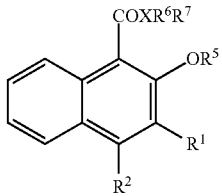

Structure D wherein X, $R^1$, $R^2$, $R^5$, $R^6$ and $R^7$ remain as defined above for Structure A.

145. The pharmaceutical composition of claim 141 wherein said organic acid is defined as

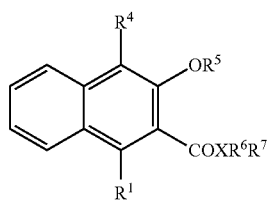

Structure E wherein X, $R^1$, $R^4$, $R^5$, $R^6$ and $R^7$ remain as defined above for Structure A.

146. The pharmaceutical composition of claim 141 wherein said organic acid is defined as

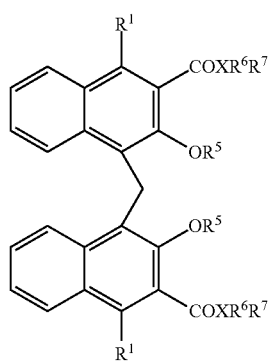

Structure F wherein X, $R^1$, $R^5$, $R^6$ and $R^7$ are independently defined as above for Structure A.

147. The pharmaceutical composition of claim 141 wherein said organic acid is defined as

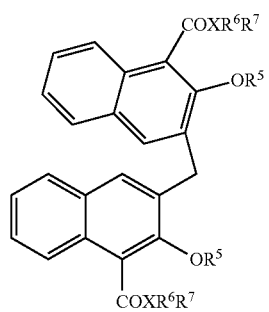

Structure G wherein X, $R^5$, $R^6$ and $R^7$ are independently defined as above for Structure A.

148. The pharmaceutical composition of claim 34 wherein said organic acid is selected from the group consisting of pamoic acid, disodium pamoate, di-ammonium pamoate, di-potassium pamoate, di-alkyl and/or di-aryl amine pamoate, di-alkyl and/or di-aryl esters of pamoic acid, and di-alkylacyl and/or di-arylacyl O-esters of pamoic acid.

149. The pharmaceutical composition of claim 148 wherein said organic acid is selected from the group consisting of pamoic acid and disodium pamoate.

150. The pharmaceutical composition of claim 34 wherein said thyroid hormone and said organic acid are in a stoichiometric ratio of 1:1 to 2:1.

151. The pharmaceutical composition of claim 34 wherein said thyroid hormone and said organic acid are in a stoichiometric ratio of 1:1.

152. The pharmaceutical composition of claim 34 wherein said thyroid hormone and said organic acid are in a stoichiometric ratio of 2:1.

153. The pharmaceutical composition of claim 34 comprising 25-300 µg of said thyroid hormone.

154. The pharmaceutical composition of claim 34 in a form selected from a pill, a tablet, a capsule, a solution, a suspension injection dose, a transdermal patch and an inhalation formulation.

155. A drug product comprising said pharmaceutical composition of claim 34.

156. The pharmaceutical composition of claim 34 further comprising at least one additive selected from an excipient, a processing aid and a buffer.

157. The pharmaceutical composition of claim 34 wherein said salt comprises liothyronine pamoate with a differential scanning calorimetry thermogram of FIG. 1.

158. The pharmaceutical composition of claim 34 wherein said salt comprises liothyronine pamoate with a Fourier Transform Infrared spectrum of FIG. 2.

159. The pharmaceutical composition of claim 34 wherein said salt comprises liothyronine pamoate with a Powder X-Ray Diffraction diffractogram of FIG. 3.

160. The pharmaceutical composition of claim 34 wherein said salt comprises liothyronine pamoate with a proton nuclear magnetic resonance spectrum of FIG. 4.

161. The pharmaceutical composition of claim 34 wherein said salt comprises liothyronine pamoate with a high pressure liquid chromatograph chromatogram of FIG. 5.

162. The pharmaceutical composition of claim 34 wherein said comprises levothyroxine pamoate with a differential scanning calorimetry thermogram of FIG. 9.

163. The pharmaceutical composition of claim 34 wherein said salt comprises levothyroxine pamoate with a Fourier Transform Infrared spectrum of FIG. 10.

164. The pharmaceutical composition of claim 34 wherein said salt comprises levothyroxine pamoate with a Powder X-Ray Diffraction diffractogram of FIG. 11.

165. The pharmaceutical composition of claim 34 wherein said salt comprises levothyroxine pamoate with a proton nuclear magnetic resonance spectrum of FIG. 12.

166. The pharmaceutical composition of claim 34 wherein said salt comprises levothyroxine pamoate with an HPLC chromatogram of FIG. 13.

167. The pharmaceutical composition of claim 34 wherein said salt of a thyroid hormone is selected from the group consisting of levothyroxine pamoate and liothyronine pamoate.

* * * * *